United States Patent [19]

Sekine et al.

[11] Patent Number: 5,347,327
[45] Date of Patent: Sep. 13, 1994

[54] PROCESS AND APPARATUS FOR MEASURING AXIAL EYE LENGTH

[75] Inventors: Akihiko Sekine; Fumio Ohtomo, both of Tokyo, Japan

[73] Assignee: Kabushiki Kaisha Topcon, Tokyo, Japan

[21] Appl. No.: 868,565

[22] Filed: Apr. 15, 1992

[30] Foreign Application Priority Data

Apr. 15, 1991 [JP] Japan .................................. 3-82657
Apr. 22, 1991 [JP] Japan .................................. 3-90877

[51] Int. Cl.$^5$ .............................................. A61B 3/10
[52] U.S. Cl. .................................. 351/211; 351/205; 351/221; 351/246
[58] Field of Search ............... 351/205, 211, 213, 221, 351/246, 215

[56] References Cited

U.S. PATENT DOCUMENTS 4,764,006  8/1988  Hamano et al. ..................... 351/211
4,938,584  7/1990  Suematsu et al. ................... 351/211
5,042,938  8/1991  Shimozono ......................... 351/205
5,141,302  8/1992  Arai et al. .......................... 351/205

*Primary Examiner*—William L. Sikes
*Assistant Examiner*—David R. Parsons
*Attorney, Agent, or Firm*—Finnegan, Henderson, Farabow, Garrett & Dunner

[57] ABSTRACT

A process and apparatus for measuring an axial eye length takes the steps of projecting monochromatic coherent light of which wavelengths are variable onto an eye to be tested, causing an interference between reflected light from a retina of the eye and reference light corresponding to the retina to generate interference signals while reflected light from a cornea of the eye is interfered with reference light corresponding to the cornea to generate interference signals, mixing these interference signals to generate beat signals while varying the wavelength, and measuring an axial eye length based on the beat signals.

8 Claims, 16 Drawing Sheets

FIG. 3(A)
WAVELENGTH VARYING DURATION
$\lambda$, $\Delta\lambda$, $t_m$, $t$
FIG. 3(B)
$A\cos(2\pi 1 e y e t + (\psi_1 - \psi_2)/2)\cos(2\pi f_0 t + (\psi_1 + \psi_2)/2)$
FIG. 3(C)
FIG. 3(D)
$A\cos(2\pi 1 e y e t + (\psi_1 - \psi_2)/2)$
FIG. 3(E)
FIG. 3(F)
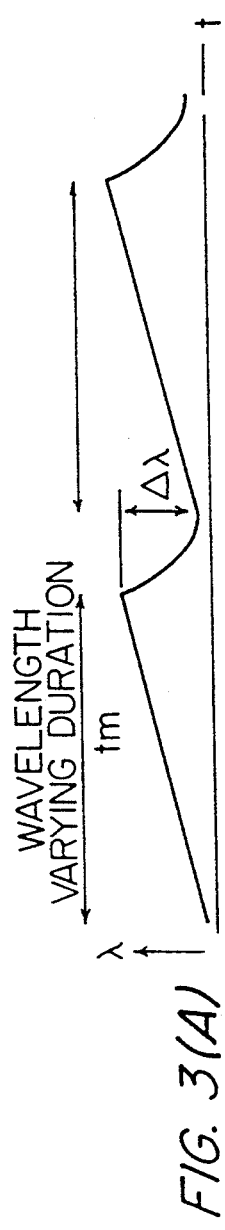

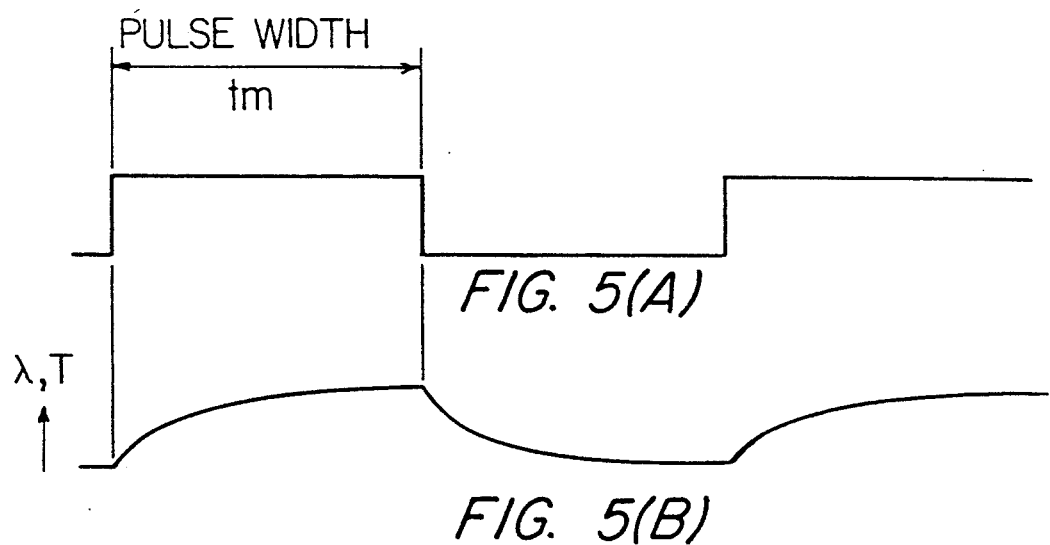
FIG. 5(A)
FIG. 5(B)
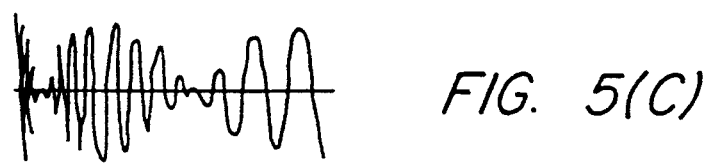
FIG. 5(C)
FIG. 5(D)
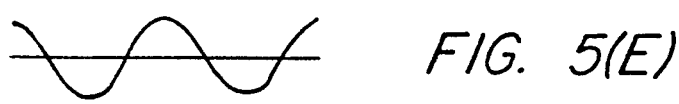
FIG. 5(E)
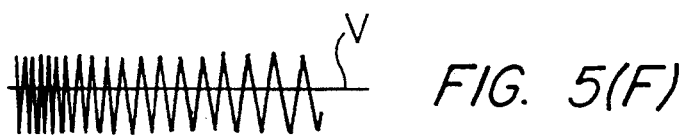
FIG. 5(F)
FIG. 5(G)
TRIGGER SIGNAL

PROCESS AND APPARATUS FOR MEASURING AXIAL EYE LENGTH

BACKGROUND OF THE INVENTION

1. Field of the Invention

This invention relates to a process and apparatus for measuring an axial eye length in which monochromatic coherent light, of which wavelength varies is projected onto an eyeball to be tested. Reflected light from a retina of the eye is interfered with reference light corresponding to the retina to obtain interference signals while reflected light from a cornea of the eye interferes with reference light corresponding to the cornea to obtain interference signals. These interference signals are mixed to produce beat signals while varying the wavelength, and an axial eye length is obtained based on the beat signals.

Further, this invention relates to a process and apparatus for measuring an axial eye length in which a laser beam emitted from a laser source of which oscillation wavelengths vary is split into measuring laser beam of light and reference laser beam of light. The measuring laser beam of light is projected onto the eye, and light reflected from the cornea of the eye interferes with light reflected from the retina of the eye. The axial length of an eye is obtained based on the interference light.

2. Description of the Prior Art

Heretofore, there has been an apparatus for measuring an axial eye length in which coherent light emitted from a laser diode is projected onto an eye to be tested, reflected lights from the retina and cornea interfere with each other for photoelectric transfer, and an axial eye length is calculated based on photoelectric transfer signals.

However, the conventional apparatus has drawbacks in that too strong coherent light must not be projected onto the eye because it causes inflammations of the retina or damage thereto, intensive interference light cannot be obtained because the reflectances of the retina and cornea are lower, or adequate photoelectric transfer signals in S/N (signal-to-noise) ratio cannot be obtained because the photoelectric transfer signals based on the interference light are too weak. Further, the photoelectric transfer signals are inconstant due to the optically coarse surface of the retina, and a clear distinction between the signals and noises is seldom made due to a weakness of the signals. Hence it is difficult to measure the axial eye length accurately.

SUMMARY OF THE INVENTION

An object of the present invention is to provide a process and apparatus for measuring an axial eye length in which measured values can be easily and correctly obtained without enhancing the intensity of coherent light needlessly, or irrespective of weak lights reflected from the retina and the cornea.

To overcome the drawbacks, a process for measuring an axial eye length according to the present invention is characterized in that monochromatic coherent light of which a wavelength is a variable is projected onto an eyeball, light reflected from a cornea interferes with reference light corresponding to the cornea to obtain photoelectric transfer signals while light reflected from a retina interferes with reference light corresponding to the retina to obtain photoelectric transfer signals, beat signals are formed by varying the wavelength of the coherent light and by mixing the photoelectric transfer signals with each other, and an axial eye length is measured based on the beat signals.

Another apparatus for measuring an axial eye length according to the present invention includes:

a measuring optical system having a coherent light source for projecting monochromatic coherent light of which a wavelength is a variable onto an eyeball;

the measuring optical system including:

a retina optical system for projecting coherent light onto a retina in the form of beams of light split by means of a beam splitter and for receiving light reflected from the retina, the retina optical system including a reference surface corresponding to the retina, and a light receiver for receiving interference light based on the reflected light from the retina and reference light corresponding to the retina;

a cornea optical system for projecting coherent light onto a cornea and for receiving light reflected from the cornea, the cornea optical system including a reference surface corresponding to the cornea, and a light receiver for receiving interference light based on the reflected light from the cornea and reference light corresponding to the cornea; and an axial eye length being calculated based on beat signals which are produced by varying the wavelength of the coherent light and inputting interference signals from the light receiver to a mixer.

According to the measuring process and apparatus of the present invention, interference information including position information of the cornea can be obtained by making interference between the reflected light from the cornea and the reference light corresponding to the cornea. Also, interference information including position information of the retina can be obtained by making interference between the reflected light from the retina and the reference light corresponding to the retina. Since the frequency of the beat signals bears a theoretically immutable relation to an axial eye length, the eye length can be calculated by mixing the two kinds of interference informations to produce the beat signals.

Further, a process for measuring an axial eye length wherein laser beam of light emitted from a laser source of which oscillation wavelengths are variable is split into measuring light and reference light, the measuring light is projected onto an eye to be tested, light reflected from the cornea of the eye and light reflected from the retina of the eye are interfered with each other, and the axial eye length is measured based on the interference light, is characterized in that:

the interference light is further interfered with the reference light, the interference light is photoelectrically transferred to obtain light receiving signals, the amount of variation of a phase difference between the reflected light from the cornea and the reflected light from the retina are educed based on the light receiving signals when the wavelength of the laser beams of light is varied within a very narrow range, and the axial eye length is measured from the amount of variation of the educed phase difference.

Further, an apparatus for measuring an axial eye length including a laser source to project laser beams of light of which oscillation wavelengths are variable, splitting means for splitting the laser beams of light into measuring light and reference light, measuring interference means for projecting the measuring light onto an eye to be tested and making interference between light reflected from the cornea of the eye and light reflected from the retina of the eye;

reference light interference means for making light interfered by the measuring interference means interfere with the reference light;

light receiving means for receiving interference light made by the reference light interference means;

phase difference detecting means for outputting phase difference signals corresponding to a phase difference between the reflected light from the cornea and the reflected light from the retina based on light signals outputted from the light receiving means;

wavelength varying means for varying the wavelength of the laser beams of light within a very small range; and arithmetic means for calculating the axial eye length of the eye based on the amount of variation of the phase difference signals outputted from the phase difference detecting means when the wavelength of the laser beams of light is varied within a very narrow range by the wavelength varying means.

Further, according to the measuring process and apparatus of the present invention, the interference light is further interfered with the reference light, the interference light is photoelectrically transferred to obtain light receiving signals, the amount of variation of a phase difference between the reflected light from the cornea and the reflected light from the retina are educed based on the light receiving signals when the wavelength of the laser beam of light is varied within a very narrow range, and the axial eye length is measured from the amount of variation of the educed phase difference.

BRIEF DESCRIPTION OF THE DRAWINGS

FIGS. 3(a)–3(f) explain waveforms of the signal of the signal processing circuit of FIG. 2.

FIGS. 5(a)–5(g) explain waveforms of the signal of the signal processing circuit of FIG. 4.

DETAILED DESCRIPTION OF THE EMBODIMENTS

The embodiments of an apparatus for measuring an axial eye length according to the present invention will be described in detail hereinafter with reference to the accompanying drawings.

Figure 1:
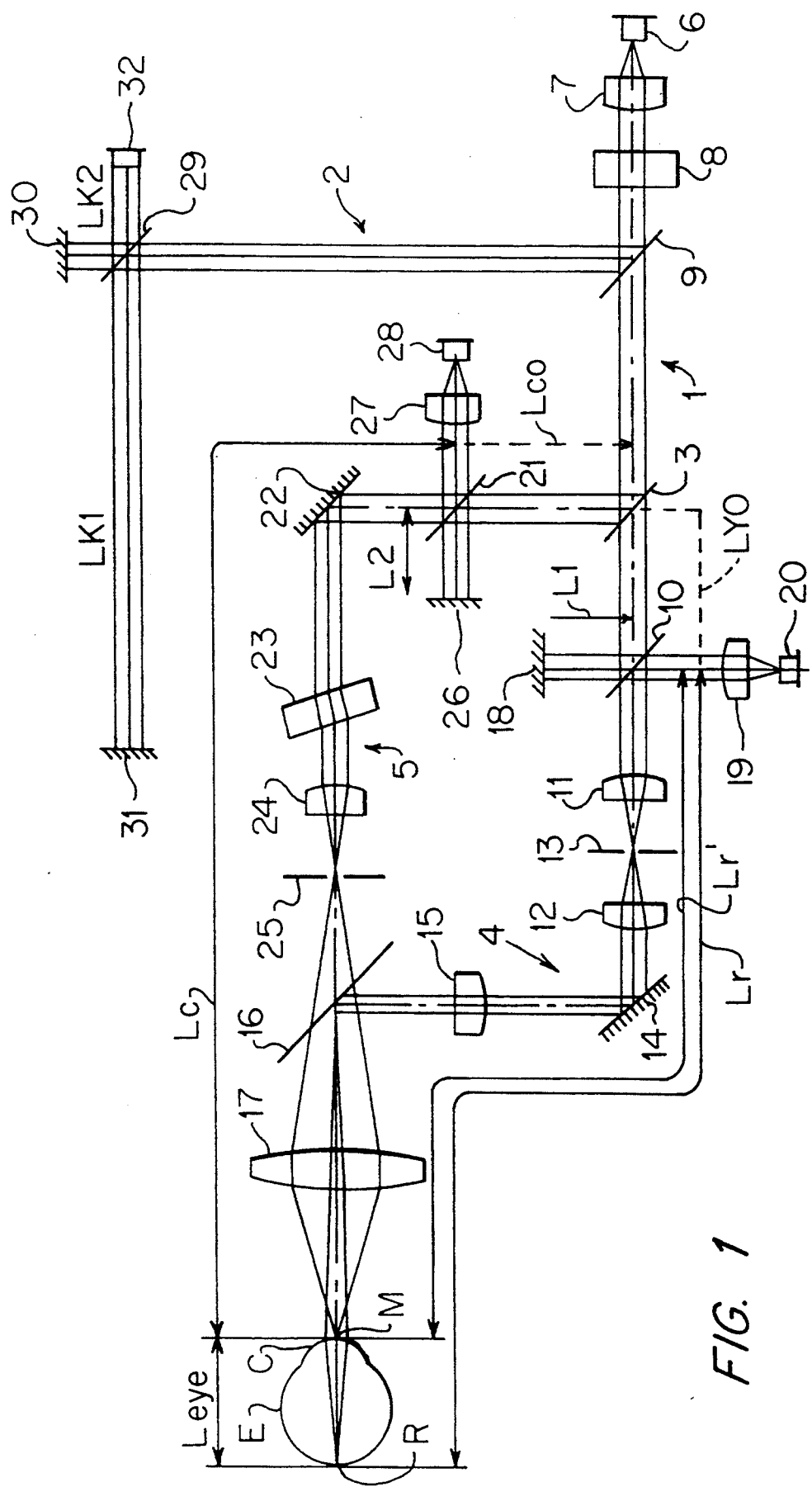
FIG. 1 is a view showing an optical system of a first embodiment of the present invention.

In FIG. 1, the numerals 1 and 2 designate a measuring optical system and a reference interference optical system, respectively. The measuring optical system 1 includes a beam splitter 3 by which the optical system 1 is split into a retina measuring optical system 4 and a cornea measuring optical system 5. The measuring optical system 1 also includes a semiconductor laser 6 to emit monochromatical coherent light. The coherent light is converted into parallel beams by means of a collimator lens 7. The parallel beams of light are guided to a beam splitter 9 via an optical light isolator 8 which serves to prevent reflected light as mentioned below from returning to the semiconductor laser 6. The semiconductor laser 6 is, therefore, preventable against modulation distortion caused by the return of the reflected light. The beam splitter 9 splits the parallel beams of light into two parts one of which is guided to the reference interference optical system 2 and the other one of which is guided to the beam splitter 3 through the beam splitter 9 as measuring light. The beam splitter 3 splits the measuring light into retina measuring light, which is guided to the retina measuring optical system 4, and cornea measuring light which is guided to the cornea measuring optical system 5.

The retina measuring optical system 4 includes a beam splitter 10, lens 11, lens 12, diaphragm 13, mirror 14, movable lens 15, beam splitter 16, objective lens 17 toward an eyeball or eye to be tested E, reference surface 18 corresponding to the retina, converging lens 19, and light receiver 20. The diaphragm 13 which serves as a low-pass filter in cooperation with the Fourier transform carried out by the lenses 11 and 12 is disposed between the lenses 11 and 12. The arrangement of the lenses 11 and 12 and diaphragm 13 is well known.

By the beam splitter 10, the retina measuring light is split in two directions. One of the split lights is guided to the reference surface 18 corresponding to the retina, reflected from the surface 18, returned along the same optical path, passed through the beam splitter 10, and converged upon the receiver 20 by the converging lens 19. The other one is passed through the lens 11, diaphragm 13 and lens 12, reflected from the mirror 14, guided to the beam splitter 16 via the movable lens 15, reflected by the beam splitter 16, and projected onto the eyeball E through the objective lens 17. The movable lens 15 serves to converge the retina measuring light upon the retina R by correcting the refracting power of the eye to be tested.

Light reflected from the retina R in turn is passed through the objective lens 17, beam splitter 16, movable lens 15, mirror 14, lens 12, and diaphragm 13, and guided to the lens 11. Scattered components included in the reflected light from the retina R are eliminated at the lens 12, diaphragm 13, and lens 11. The reflected light from the retina R is reflected by the beam splitter 10, guided to the light receiver 20, and interfered with light reflected from the reference surface 18 corresponding to the retina. The receiver 20 outputs interference signals by transforming the interference light to photoelectric signals.

The cornea measuring optical system 5, of which an optical axis is coaxial with that of the objective lens 17 by means of the beam splitter 16, includes a beam splitter 21, mirror 22, compensating plate 23 for an optical path length, lens 24, diaphragm 25, reference surface 26 corresponding to the cornea, converging lens 27, and light receiver 28. The diaphragm 25 serves as a low-pass filter in cooperation with the Fourier transform carried out by the objective lens 17 and lens 24. By the beam splitter 21, the cornea measuring light is split in two directions. One of the split lights is guided to the reference surface 26 corresponding to the cornea, reflected from the surface 26 and returned along the same optical path, passed through the beam splitter 21, and converged upon the receiver 28 by the converging lens 27.

The other one passes through the mirror 22, compensating plate 23 for an optical path length, lens 24, diaphragm 25, beam splitter 16, objective lens 17, and converged upon the apex M of the cornea C. Light reflected from the apex M of the cornea C returns along the same optical path, passed through the objective lens 17, beam splitter 16, diaphragm 25, compensating plate 23, and mirror 22, and guided to the beam splitter 21. Scattered components included in the reflected light from the cornea C are eliminated at the lens 17, diaphragm 25, and lens 24. The reflected light from the cornea C is reflected by the beam splitter 21, guided to the light receiver 28, and interfered with light reflected from the reference surface 26 corresponding to the cornea. The receiver 28 outputs interference signals by transforming the interference light to photoelectric signals. The compensating plate 23 serves for obtaining the equation $Ls = Lr' - Lc = 0$ where Lc is an optical path length between the center of the beam splitter 21 and the apex M of the cornea C, Lr' is an optical path length between the center of the beam splitter 10 and the apex M of the cornea C, and Ls is the difference between Lr' and Lc. In other words, the compensating plate 23 adjusts the two lengths Lr' and Lc to be equal.

The reference interference optical system 2 includes a beam splitter 29, mirrors 30, 31, and light receiver 32. Reference light is split into two directions by means of the beam splitter 29. The split lights are guided to the mirrors 30, 31 respectively, reflected by the mirrors 30, 31, returned along the same respective optical path, and synthesized by means of the beam splitter 29. The synthesized light is guided to the light receiver 32, the receiver 32 transforms the interference light to photoelectric signals, and reference interference signals are outputted. From this reference interference optical system 2, the following equation is obtained.

$$Lbase = 2 (LK1 - LK2)$$

where LK2 is a distance between the beam splitter 29 and mirror 30, LK1 is a distance between the beam splitter 29 and mirror 31, and Lbase is a reference optical path difference. The difference ⌈Lbase⌋ (an abbreviation thereof will be hereinafter represented as ⌈Lbase⌋) is predetermined to be adequately longer than the axial eye length ⌈Leye⌋). The reason thereof will be described below.

The semiconductor laser 6 is heated or cooled by thermometer controlling means, not shown, such as the Peltier effect type of element in order to control the wavelength of coherent light emitted from the semiconductor laser 6.

A principle for measuring the axial eye length will be now described together with a signal processing circuit.

Figure 2:
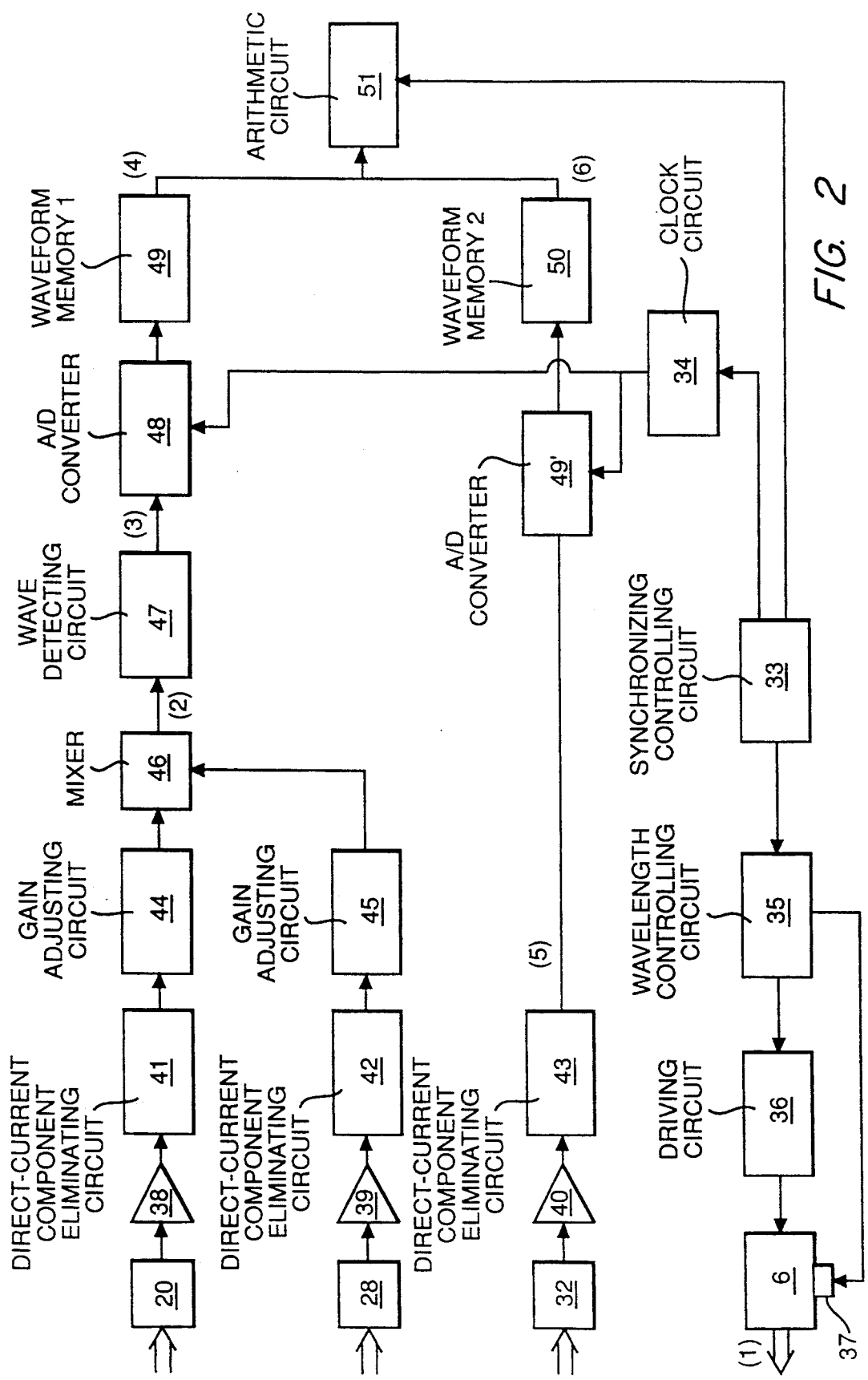
FIG. 2 is a block chart showing circuits for processing signals to obtain an axial eye length using the optical system of FIG. 1.

In FIG. 2, the numeral 33 designates a synchronization controlling circuit which outputs synchronizing signals to a clock circuit 34 and wavelength controlling circuit 35. The wavelength controlling circuit 35 outputs to a driving circuit 36 and wavelength controlling means 37.

The intensity I1 of the interference light in the light receiver 20 is theoretically subject to the following equation.

$$I1 = 2Ar \cdot Arefl \cdot \cos \{2\pi \cdot 2(Lr - L1)\lambda\} \qquad (1)\text{-}1$$

where Ar is an amplitude of the light reflected from the retina R, Aref1 is an amplitude of the light reflected from the reference surface 18 corresponding to the retina and $\lambda$ is a wavelength of the coherent light, and $2\pi \cdot 2(Lr - L1)/\lambda$ denotes the difference in phase of the interference light.

The intensity I2 of the interference light in the light receiver 8 is theoretically subject to the following equation.

$$I2 = 2Ac \cdot Aref2 \cdot \cos\{2\pi \cdot 2(Lc - L2)/\lambda\} \qquad (1)\text{-}2$$

where Ac is an amplitude of the light reflected from the cornea C, Aref2 is an amplitude of the light reflected from the reference surface 26 corresponding to the cornea, $\lambda$ is a wavelength of the coherent light, and $2\pi \cdot 2(Lc - L2)/\lambda$ denotes the difference in phase of the interference light.

In the equations (1)-1 and (1)-2, direct-current (bias) components and initial phases are omitted.

Further, the following equation is obtained.

$$Lr = Lr' + Leye$$

When the wavelength of the coherent light is continuously varied by $\Delta\lambda$, a phase difference of the interference light at the light receiver 20 is also varied to $2\pi \cdot 2(Lr - L1)/(\lambda + \Delta\lambda)$ and a phase difference of the interference light at the light receiver 28 to $2\pi \cdot 2(Lc - L2)/(\lambda + \Delta\lambda)$.

When the term of each phase difference is developed in progression (series) with the condition of $\lambda > \Delta\lambda$, the amount of variation of each phase difference is denoted as follows:

$$2\pi \cdot 2(Lr - L1)\Delta\lambda/\lambda^2, \ 2\pi \cdot 2(Lc - L2)\Delta\lambda/\lambda^2 \qquad (2)$$

Since the intensities I1 and I2 of the interference light are periodically varied at every phase difference $2\pi$, the interference signals outputted from each light receiver 20, 28 are also periodically varied in accordance with the wavelength of the coherent light. Each term in (2) represents the periodicity of the interference signals.

In this embodiment, the wavelength controlling means, as shown in FIG. 3(a) varies the wavelength $\lambda$ of the coherent light linearly with respect to time t. Let it be supposed that a period of time tm required for modulating from the wavelength $\lambda$ to $\lambda + \Delta\lambda$ one second and $\Delta\lambda/\lambda^2$ per optical path length of 1 mm is 1. The interference signals of the light receivers 20, 28, and 32 are amplified by amplifiers 38, 39, and 40, respectively and direct-current components thereof are eliminated by direct-current component eliminating circuits 41, 42, and 43 respectively.

By the above supposition, i.e., tm=1 and $\Delta\lambda/\lambda^2$ per optical path length of 1 mm=1, the following equations are obtained.

$$f1 = 2(Lr - L1) \text{ Hz} \tag{3)-1}$$

$$f2 = 2(Lc - L2) \text{ Hz} \tag{3)-2}$$

where f1 is the frequency of the interference signals corresponding to the intensity I1 of the interference light, and f2 is the frequency of the interference signals corresponding to the intensity I2 of the interference light.

Since the optical path length is generally represented as Lr=Lc+Leye+Ls (Ls=|Lr'−Lc|), the frequency f1 of the interference signals of the receiver 20 is $$f1 = 2(Lc + Leye + Ls - L1) \tag{4)-1}$$

When the optical path length compensating plate 23 is adjusted to have Ls=0 add the measuring optical system 1 is arranged to have L1=L2, the following equations are obtained.

$$f1 = 2(Lc + Leye - L1) \tag{4)-1}$$

$$f2 = 2(Lc - L1) \tag{4)-2}$$

If the relation Lc-Li>Leye is satisfied, the frequency f1 approaches the frequency f2 in value. Gain adjusting circuits 44, 45 adjust the amplitude of each interference signal, the mixer 46 mixes them, and beat signals are produced. The gain adjusting circuits 44, 45 serve adjust the contrast of the beat signals.

A beat frequency fb is fb=f1-f2=2Leye.

A synthetic frequency $f_{S18}$ is $$f_{S18} = (f1 + f2)/2 = 2Lc - 2L1 + Leye$$

Therefore, the beat signal S satisfies the following equation.

$$S = A\cos\{2\pi Leye\cdot t + (\psi 1 - \psi 2)/2\}\cdot\cos\{2\pi(2Lc - 2L1 + Leye)t + (\psi 1 + \psi 2)/2\}$$

where A is an amplitude of the beat signal, $\psi 1$ and $\psi 2$ are initial phases of the light receivers 20 and 28 respectively.

The waveform of the beat signal S is shown in FIGS. 3(B). The axial eye length ⌈Leye⌋ can be obtained according to the equation fb=2Leye by detecting the beat signal S by means of a detector circuit 47 and by obtaining the beat frequency fb. The detected waveform is shown in FIG. 3(c). If Ls does not accurately reach zero by the compensating plate 23, the eye visual length is corrected according to fb=2Leye+2Ls by subtracting the difference Ls from the measured value.

When time tm is required for the variation between the wavelength $\lambda$ and the wavelength $\lambda + \Delta\lambda$, the following equations are obtained.

$$f1 = \{2(Lc + Leye - L1)\cdot(\Delta\lambda/\lambda^2)\}/tm \tag{5)-1}$$

$$f2 = \{2(Lc - L1)\cdot(\Delta\lambda/\lambda^2)\}/tm \tag{5)-2}$$

According to (5)-1 and (5)-2, the beat frequency fb is $$fb = f1 - f2 = (2Leye\cdot\Delta\lambda/\lambda^2)/tm \tag{6}$$

Therefore, 2Leye can be calculated based on the beat frequency fb and the value $\Delta\lambda/(\lambda^2\cdot tm)$. The detected waveform is stored in a waveform memory 49 via an A/D converter 48 in which conversion timing signals are inputted from the clock circuit 34. FIG. 3(D) shows a waveform stored in the waveform memory 49.

Since it is difficult to immediately obtain the wavelength $\lambda$ and the amount of variation $\Delta\lambda$ of the wavelength, the frequency fb is related not immediately to ⌈Leye⌋ but to the frequency of the reference interference signals obtained by the reference interference optical system 2.

When the wavelength is varied from $\lambda$ to $\lambda + \alpha\lambda$, the amount of variation $\Delta\delta$ base of the phase difference of the reference interference optical system 2 is $$\Delta\delta base = (2\pi\cdot 2Lbase\cdot\Delta\lambda/\lambda^2)tm$$

After eliminating direct-current components (see FIG. 3(E)), the reference interference signals are also stored in a waveform memory 50 via an A/D converter 49'. Timing signals from the clock circuit 34 are inputted in the A/D converter 49'. A waveform stored in the waveform memory 50 is shown in FIG. 3(F).

If the reference interference signals of the frequency ⌈fbase⌋ are obtained from the receiver 32 with both the values $\lambda$ and $\Delta\lambda$ unknown, the following equation is obtained:

$$fbase = (2Lbase\cdot\Delta\lambda/\lambda^2)/tm \tag{7}$$

Therefore, according to (7), the frequencies f1 and f2 are $$f1 = fbase\cdot 2(Lc + Leye - L1)/2Lbase$$

$$f2 = fbase\cdot 2(Lc - L1)/2Lbase$$

Therefore, the beat frequency fb of the interference signal is obtained by the following equation:

$$fb = fbase\cdot 2Leye/2Lbase \tag{8}$$

Accordingly, by measuring the beat frequency fb, the axial eye length can be calculated by the following equation (9)-1 which is transformed from the equation (8).

$$Leye = (Lbase\cdot fb)/fbase \tag{9)-1}$$

The beat frequency fb and the reference frequency ⌈fbase⌋ are obtained as follows.

During the wavelength variation period of time tm, the interference signals and the reference interference signals are stored in the waveform memories 49 and 50 respectively. If a clock timing frequency of waveform data to the waveform memories 49 and 50 is defined as fad, the number of data during the wavelength variation period of time tm is represented as N=fad·tm.

By calculating the number of data ns included in one cycle of the reference interference signals the frequency ⌈fbase⌋ of the reference interference signals can be obtained. Namely, $$fbase = fad/ns \tag{9)-2}$$

Therefore, regardless of the frequency ⌈fad⌋ of the clock signals being unknown, fb/fbase in the equation (9)-1 can be obtained by simultaneously attaining the reference interference signals and the beat signals while synchronizing with the clock signals and by applying the equation (9)-2 to the beat frequency, as follows:

$$fb/fbase = nbs/ns$$

where nbs is a periodicity of the beat signals during a wavelength variation time period tm. If the sum N of data for the wavelength variation period of time is constant, ns is determined according to the periodicity nbase of the reference interference signals for the time period tm.

Accordingly, N (the sum of data of the reference interference signals for a wavelength variation period of time), ns (the number of data included in one cycle of the reference interference signals), and nbase (the frequency of the reference interference signals for the wavelength variation time period tm) each satisfies the following equation.

$$N = ns \cdot nbase$$

N also represents the sum of data of the interference beat signals and the following equation is obtained.

$$N = nb \cdot nbs$$

where nb is the number of data in one cycle of the beat signals.

Accordingly, it is led to the following equations.

$$nbs/ns = nbase/nb$$

$$fb/fbase = nbase/nb$$

According to either of these two equations, an arithmetic circuit 51 calculates the visual eye length.

Since the beat frequency fb is related to the eye length ⌈Leye⌋, the apparatus has a dull sensitivity to the misalignment and the motion of the eyeball, especially the motion of the head of a person to be tested.

In other words, when Lr and Lc are each varied by ΔL owing to the misalignment, the signal frequencies f1 and f2 for the wavelength variation time tm are each varied as follows:

$$f1 = \{2(Lr + \Delta L - L1) \cdot \Delta\lambda/\lambda^2\}/tm$$

$$f2 = \{2(Lc + \Delta L - L2) \cdot \Delta\lambda/\lambda^2\}/tm$$

The synthetic frequency $f_{SI8}$ is varied in response to them.

$$f\phi = \{(2Lc - 2L1 + Leye + \Delta L) \cdot \lambda/\lambda^2\}/tm$$

However, since both f1 and f2 are simultaneously varied by the same amount, the beat frequency fb remains constant.

Preferably, the frequencies of fe and fb are, therefore, kept fully apart from each other in value and a circuit is arranged where the beat frequency can be easily measured in response to the variation of the synthetic frequency $f\phi$.

As shown in the equation (1)-1 since the amplitude of the interference light is determined by multiplying the amplitude of the measuring light by that of the reference light, the signal amplitude of the interference light can become enlarged according to the amplitude of the reference light.

In order to explain the principle for measuring the axial eye length, there has been hereinbefore described an embodiment where the wavelength of the coherent light of the semiconductor 6 is linearly varied with respect to time.

A more preferable embodiment will be described because it is difficult to control the wavelength of the coherent light so as to be linearly varied with respect to time.

Figure 4:
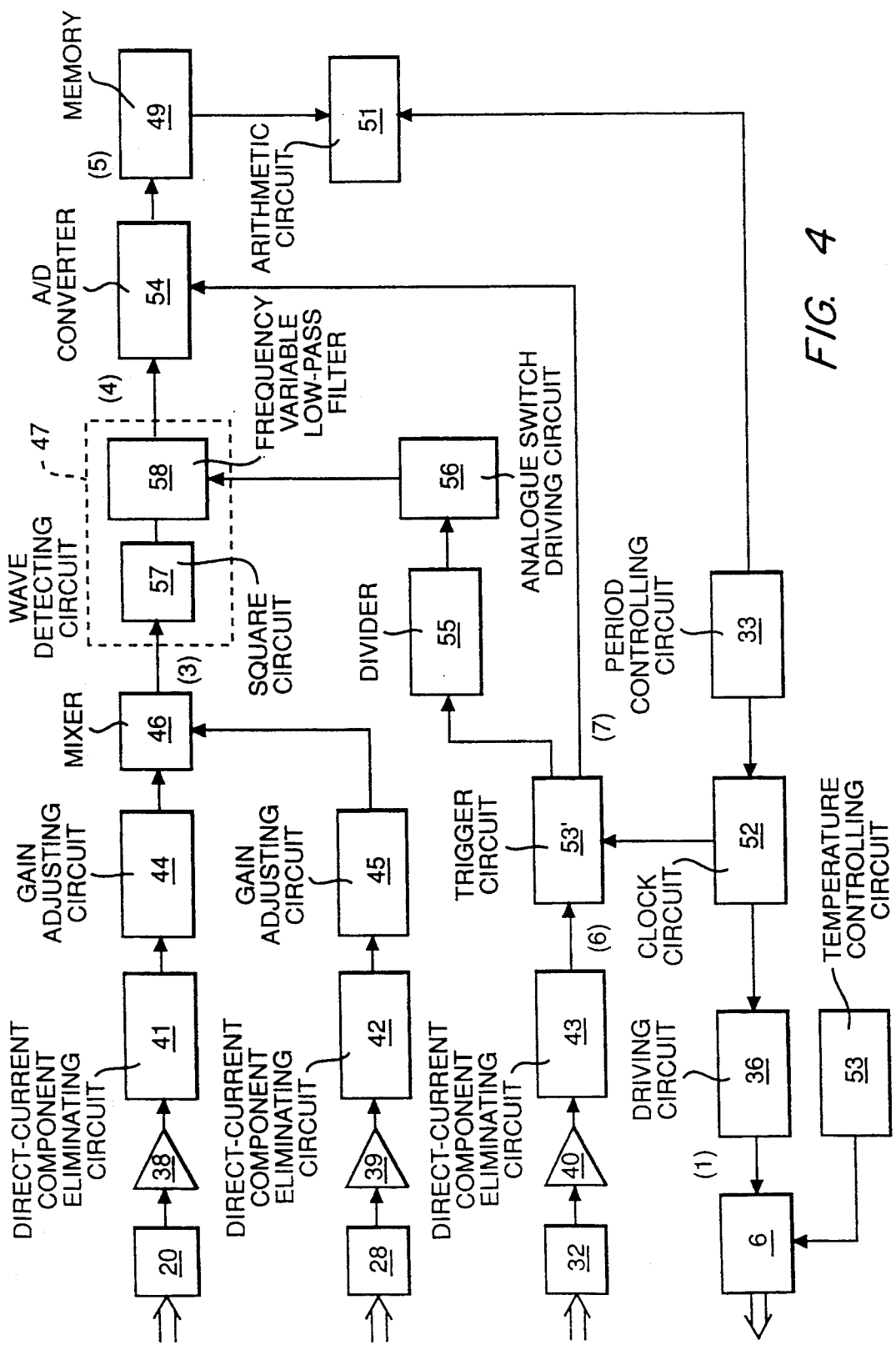
FIG. 4 is a block chart showing a signal processing circuit of another embodiment.

In this embodiment, the semiconductor laser 6 is driven like a pulsed laser and the wavelength of the coherent light is nonlinearly varied with respect to time. In FIG. 4, the numeral 52 denotes a clock controlling circuit, which is controlled by a synchronous controlling circuit 33. A driving circuit 36 is controlled by the clock controlling circuit 52, it outputs rectangular pulse electric current (see FIG. 5(A)), and it drive the semiconductor laser. When the rectangular signals are inputted and turned on, the semiconductor laser 6 begins to oscillate and a chip temperature T thereof rises as shown in FIG. 5(B). The oscillating wavelength is varied according to the variation of the chip temperature of the semiconductor laser 6. Except for the mode hop (or mode jump) position, the temperature and wavelength correspond to each other in ratio of one to one. The variation of the output of the oscillation is very slight and negligible as compared to the variation of the wavelength.

The greatest variation in temperature is brought about immediately after the oscillation and it gradually calms down. After a given period of time, the semiconductor laser 6 is turned off to be returned to the former temperature and the projection of the coherent light is stopped. The width of the rectangular pulses is determined in relation to the width Δλ of the wavelength variation. When the semiconductor laser 6 is pulsed at about 1 KHz example, the main characteristic portions of the wavelength variation can be used or reproduced.

The semiconductor laser 6, of which a mode hop distance is longer than the width of the wavelength variation, is used and the reference temperature of the laser 6 is controlled by a temperature controlling circuit 53 as shown in FIG. 4.

The wavelength variation corresponds to the temperature variation and it is nonlinear so as to be greatly varied at the beginning and be gradually calmed down. Corresponding to the variations of the wavelength and temperature, the frequency ⌈fbase⌋ of the reference interference signals, the frequencies f1 and f2 of the interference signals, and the beat frequency fb are also varied. The beat signal S is varied as shown in FIG. 5(C).

Therefore, by A/D-transferring these interference and mixing signals with a constant trigger circuit in frequency, data are stored in which the frequency is high in the beginning and gradually decreased.

According to Eq. (8), the following equation is obtained.

$$fb = fbase \cdot Leye/Lbase$$

The above equation means that fb equals the multiple of ⌈base⌋ when ⌈Leye⌋ and ⌈bas⌋ are both constant within a wavelength variation period tm.

Therefore, a trigger signal as shown in FIG. 5(G) is outputted by slicing the reference interference signal (see the waveform of FIG. 5(F)) of the frequency ⌈fbase⌋ by a given threshold value V belonging to a trigger circuit 53'. This trigger signal is used as a transfer timing signal of an A/D converter 54. The trigger signal is also inputted in an analog switch driving circuit 56 via a frequency divider 55. The analog switch driving circuit 56 serves to transfer a cutoff frequency of a frequency varying low-pass filter 58. The low-pass filter 58 and a square circuit 57 compose a detection circuit 47. The low-pass filter 58 is used to carry out the wave detection accurately. The reason is that an accurate detection may not be carried out since the beat frequency fb is probably higher than the synthetic frequency f$\phi$ at the beginning and end of the wavelength variation period tm and the mixing signal of f$\phi$ is passed through at the end of tm when arranged to pass the beat at the beginning of tm.

Figure 6:
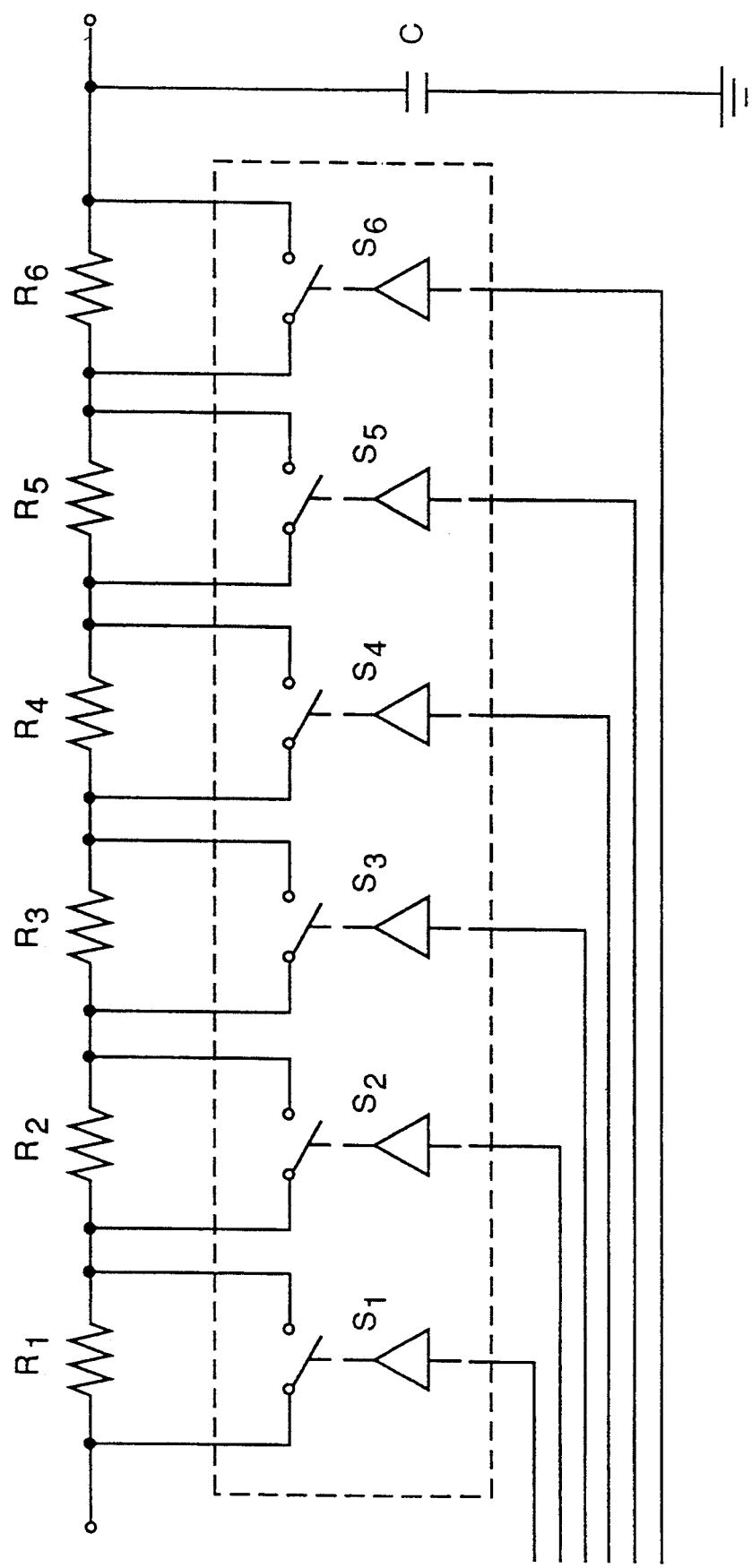
FIG. 6 is a view showing a low-pass filter.

The frequency varying low-pass filter 58 varies the cutoff frequency corresponding to the wavelength variation. As shown in FIG. 6, the low-pass filter 58 includes resistances R1, R2, . . . , R6, which are each different in value and are arranged in series, analog switches S1, S2, . . . , S6, which are each connected to the resistances in parallel and from short circuits access corresponding resistances, and a capacitor C. The analog switch driving circuit 56 serves to turn on or off the analog switches S1, S2, . . . , S6. When the resistance values of R1 to R6 are set in the ratio of 3., 2, 4, 8, 16, and 32, respectively, and in 6-bit, the cutoff frequency fcut is $$fcut = Constant \times (1/C \cdot R)$$

where C is a capacitance of the capacitor C, R is a synthetic resistance.

Figure 7:
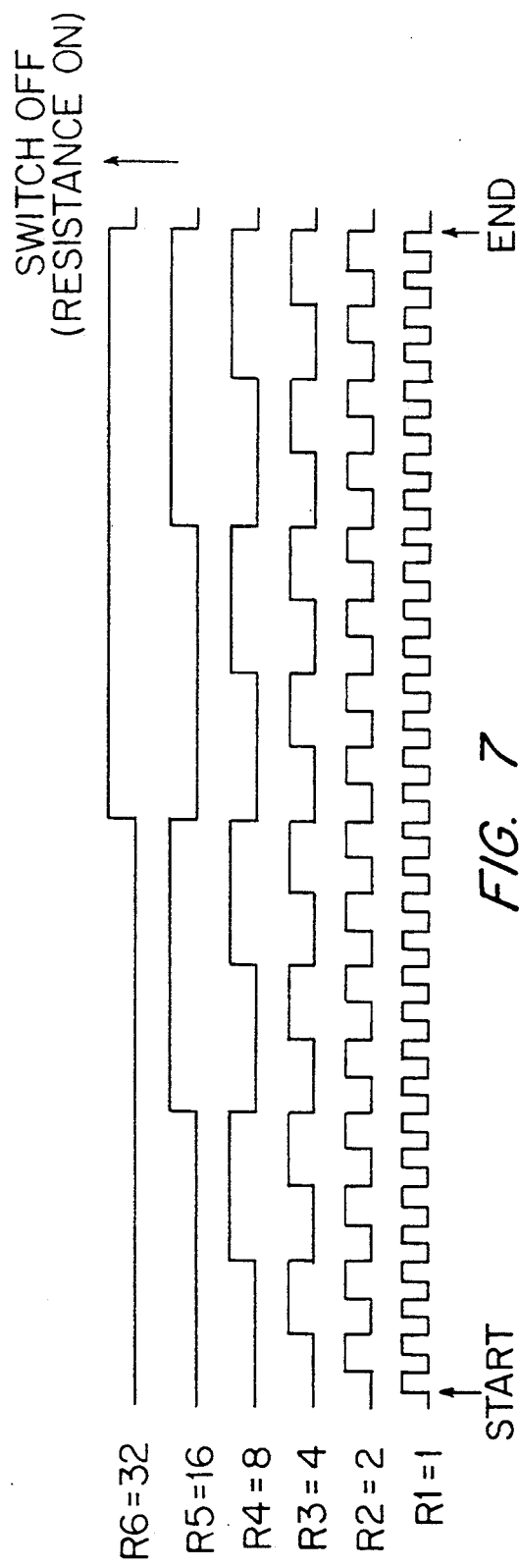
FIG. 7 is a timing chart for explaining the function of a frequency divider.
Figure 8:
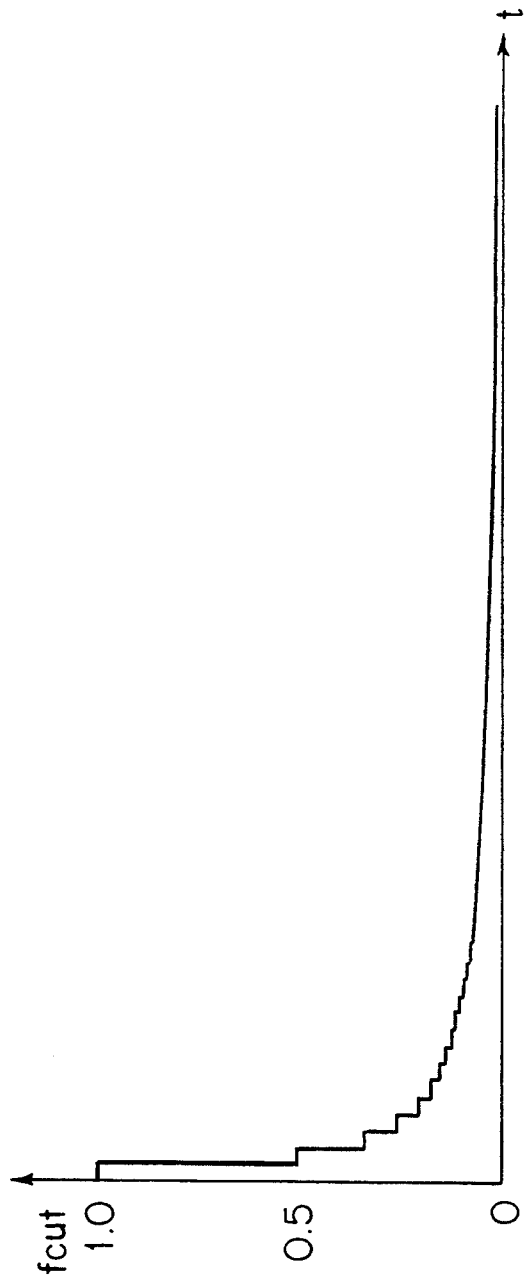
FIG. 8 is a graph showing the variation of a cutoff frequency.

Therefore, the cutoff frequency is set to be high at the beginning and decreased accordingly as the frequency of the reference interference signal decreases. The resistance corresponding to 1 of the above ratio is the turned off state, the maximum value of fcut is predetermined 1, and it can be varied from 1 to 1/63 by turning off all the analog switches. The cutoff frequency is varied as shown in FIG. 8 by outputting the dividing signal from a dividing circuit 65 as shown in FIG. 7.

After passing through the detection circuit 47, the signal (see the waveform FIG. 5(D)) is inputted in the A/D converter 54, which obtains data by using the trigger signal as shown in FIG. 5(G) in the form of a timing signal. As shown in FIG. 5(G), the trigger signal varies the interval for producing it in accordance with the frequency variation. Since the frequency of the beat signal transferred by the A/D converter 54 is varied such that the ratio of the beat frequency to the frequency of the reference interference signal is constant, the waveform stored in the waveform memory 49 via the A/D converter 54 is in appearance cyclic. Therefore, the waveform as shown in FIG. 5(E) is stored in the memory 49. The number of data included in one cycle of the obtained signal is fbase/fb.

Therefore, according to the equation fb=fbase. Leye/Lbase, the axial eye length is Leye=Lbase/(the number of data in a cycle)

In the above embodiment, it has been described that the cornea reflection light passes through only the cornea measuring optical system 5 while the retina reflection light returns through only the retina measuring optical system 4. However, any other reflected light described below may be mixed with them. A part of the retina reflection light produced by the retina measuring optical system 4 is reflected from the cornea and the retina reflection light near the optical axis returns through the cornea measuring optical system 5 to the light receiver 28 ( this reflected light is hereinafter referred to as R1'). Similarly, a part of the cornea projecting light by the cornea measuring optical system 5 reaches the retina and it is reflected therefrom to return through the retina measuring optical system 4 to the light receiver 20 ( this reflected light is hereinafter referred to as R2'). Further, each part of the retina and cornea reflection lights returns through the cornea and retina measuring optical systems 5 and 4 to the light receivers 28 and 20, respectively, (the reflected light to the receiver 28 is hereinafter referred to as R3' and the reflected light to the receiver 20 as R4'). The mixed light of R1' and R3' and the mixed light of R2' and R4' interfere with the normal reflection light. When each phase of the cornea and retina projecting lights is coincided with each other at the apex of the cornea, the phase difference between R1' and normal cornea reflection light R5' equals zero in the light receiver 28 and the phase difference between R3' and R5' equals 2Leye in the light receiver 28, while the phase difference between R2' and normal retina reflection light R6' equals zero in the light receiver 20 and the phase difference between R4' and R6' equals 2Leye in the light receiver 20. In other words, the phase differences produced by variously mixing the reflection lights are related to the visual eye length. When the signal is allowed to beat, it is limited to the combination of the beat signal of the frequency fb, the signal of the synthetic frequency f$\phi$ as described after the equations (4)-1 and (4)-2, and the noise signal of the same frequency fb as the frequency fb of the beat signal (except electric noises).

Therefore, although the noise signal of all the signals after detection is a little modulated, the signal after detection is composed of signal components of which each frequency is the same. When the reflected light noise is mixed, the optical system is arranged so that the optical path length Lr0 between the beam splitters 3 and 10 and the optical path length Lc0 between the beam splitters 3 and 21 become equal, Lr' equals Lc, and L1 equals L2. In such an optical system, the axial eye length can be obtained by processing the same as in the case of no noise.

Although the invention has been explained in relation to the above embodiment, it is to be understood that the following modifications and variations can be made without departing the spirit and scope of the invention as hereinafter claimed.

(1) A polarized light beam splitter and P-polarized light are used in place of the beam splitter 16 and the incident light to the beam splitter 4, respectively. When a λ/2 plate is inserted in the optical path of tile retina optical system 4 situated immediately after the beam splitter 3 and a polarized-light surface thereof is rotated by 90°, the measuring light toward the cornea optical path 5 is converted into P-polarized light and the measuring light toward the retina optical path 4 is converted into S-polarized light. Such an arrangement can lessen a loss in the amount of light caused by the beam splitter 16 because the cornea and retina reflections each tend to reserve the polarized light. Further, the optical noises can be decreased regardless of the trespass of the reflected lights from the cornea and retina on the different optical path because P-polarized light does not interfere with S-polarized light. Further, the optical path length difference between Lr' and Lc does not need to be completely made zero, and it can be corrected by subtracting the difference Ls from the measured value.

(2) When polarized light is used in such a manner as in (1), P-polarized light for the cornea and S-polarized light for the retina are simultaneously, as each light is, introduced to a sole light receiver by relating the lights introduced to the light receivers 20 and 21. Since P and S polarized lights do not interfere with each other, an interference fringe between the cornea reflection light and the reference light for the cornea, and an interference fringe between the retina reflection light and the reference light for the retina are independently varied in intensity. Beat signals are outputted by photoelectrically transferring the sum of the intensities of the interference fringes.

(3) In the above embodiments, reflected light in which light is converged upon the apex M of the cornea and is reflected therefrom is used. Supposing that the cornea surface is spherical, any other point such as the center of curvature would be found where the reflected light from the cornea passes through the diaphragm 25. That is, if light is converged upon the center of the sphere, the reflected light from the cornea which passes through the diaphragm 25 can interfere with the reference light because the reflected light goes back along the same path. This means that the axial eye length can be measured at two different points with a single apparatus. In the first embodiment, the reflected light goes forward through the diaphragm 25 to the light receiver 28 when a virtual image formed by the retina projecting light coincides with a point conjugate with the diaphragm 25. If such an arrangement as described in the end paragraph of the first embodiment description is carried out, the axial eye length can be also measured with the reflected light.

(4) In all the embodiments as explained hereinbefore, an arrangement is commonly made wherein the identical optical system is used for projecting coherent light onto the retina or cornea of the eye to be tested and for receiving light reflected from the retina or cornea. However, it is possible to separate the projecting and receiving optical systems. One example of such a system is shown in FIG. 9 in which a reference interference optical system 2 is not shown.

Figure 9:
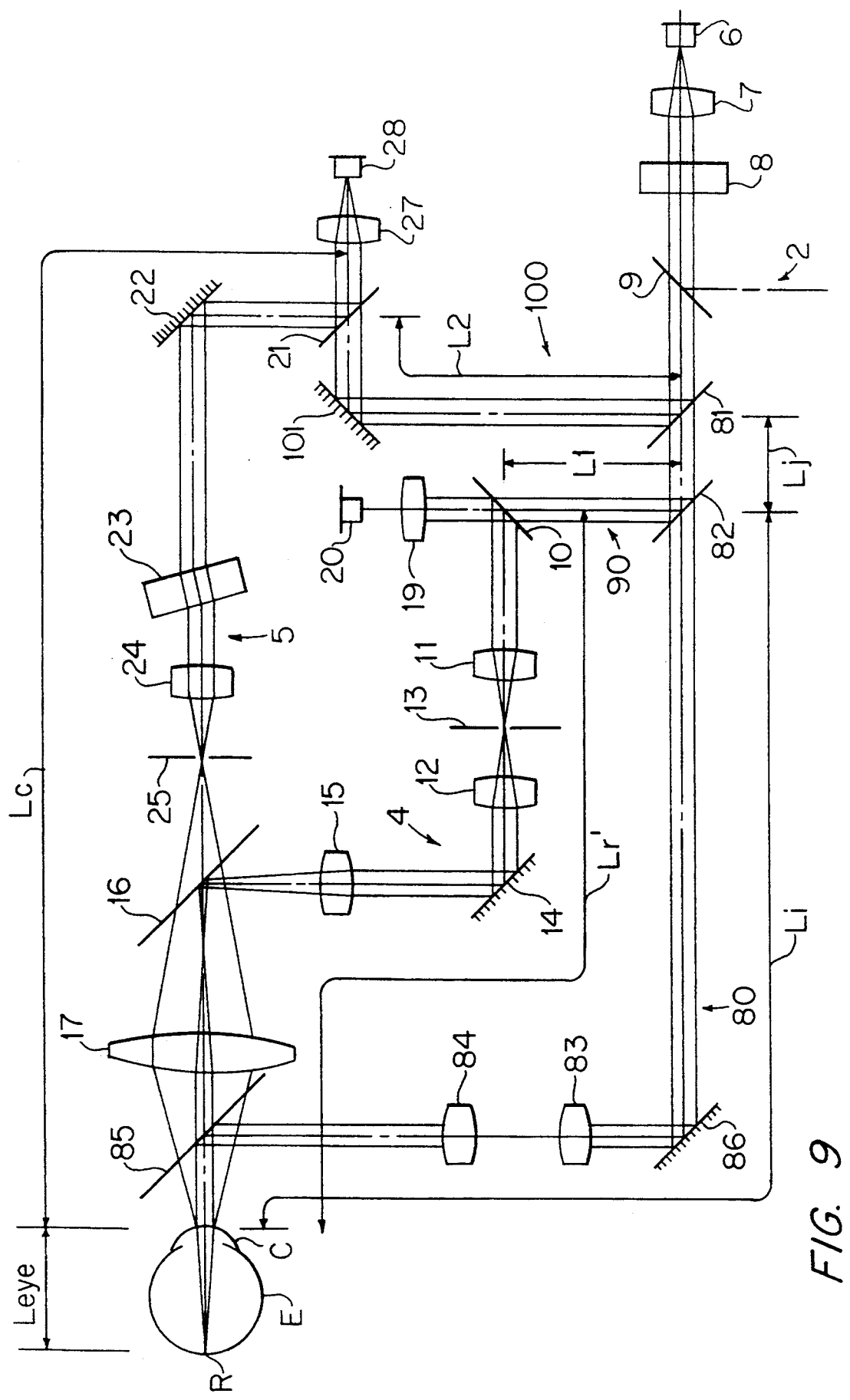
FIG. 9 is a view showing an optical system of a variant of the first embodiment.

In FIG. 9, a projecting optical system 80 is used in common for the retina and cornea, and is provided with refracting power correcting lenses 83 and 84. The coherent light is projected in such beams of light as to correct the refracting power of the eye and be converged upon the retina. One part of the beams of light is reflected from the cornea surface as divergent light and the other part is reflected from the retina. Of these reflected lights, the light which passes through a light splitting member 85 are introduced into a reflected light receiving optical system and are split into the optical system 4 for the retina and the optical system 5 for the cornea. The reference light is introduced into both the optical systems 4 and 5 from any point within the projecting optical system, it is interfered with the retina and cornea, it is received' by the light receivers 20 and 28, and each output from the receivers is mixed with each other to obtain beat signals. Amendments to the corresponding equations are, however, required because the optical path length difference, for example, is different from those in the other embodiments. The phase difference of the interference light received by the receiver 20 is $$2\pi(Li+2Leye+Lr'-L1)/\lambda$$

and the phase difference of the interference light received by the receiver 28 is $$2\pi(Lj+Li+Lc-L2)/\lambda$$

where Li is an optical path length between the center of the beam splitter 82 and the cornea, Lr' is an optical path length between the cornea and the beam splitter 10, Lj is an optical path length between the beam splitters 81 and 82, and L1 and L2 are optical path lengths of reference light optical path corresponding to the retina 90 and reference light optical path corresponding to the cornea 100, respectively. Similar to the above embodiments, an arrangement having the equations Lr'=Lc and Li=L2−Lj is carried out to obtain the difference 2Leye.

It may be noted that the reflected light from the cornea surface is under illusions emitted from neither the apex of the cornea nor the center of curvature of the cornea. In other words, when the diaphragm 25 become conjugate with the virtual image formed by the reflected light from the cornea, the reflected light can pass through the diaphragm 25. However, since there is only one projecting light and R1' and R2' of the reflected lights causing the noises as mentioned above are not produced, the same measurement as in the first embodiment can be carried out.

A second embodiment will be now described hereinafter with reference to FIG. 10. An optical arrangement of the reference optical system 2 in this embodiment is the same as that in the first embodiment. The reference optical path difference ⌈Lbase⌋ is arranged sufficiently longer than the axial eye length ⌈Leye⌋ similar to the first embodiment. Total reflection mirrors 30 and 31 serve as a reference object and a reference surface corresponding to the reference object, respectively.

A light receiver 32 serves as a first light receiving means. The measuring optical system 1 includes the semiconductor laser 6, collimator lens 7, optical isolator 8, and beam splitter 9 as in the first embodiment. The semiconductor laser 6 is controlled by the same temperature controlling means as in the first embodiment. Laser beam from the laser 6 passes through the beam splitter 9 and is guided to a beam splitter 150. The beam splitter 150 splits the laser beam into a measuring laser beam of light and a reference laser beam of light. The reference laser beam is guided to a reference optical system 500. The measuring light is guided to the beam splitter 3 as in the first embodiment. The beam splitter 3 splits the measuring laser beam of light into a laser beam for the cornea and a laser beam for the retina as in the first embodiment. The laser beam for the retina is guided to a retina illuminating optical system 4' corresponding to the retina measuring optical system 4. The laser beam for the cornea is guided to a cornea illuminating optical system 5' corresponding to the cornea measuring optical system 5. Numeral 400 denotes an interference light receiving optical system for receiving interference light. Interference measuring means include the beam splitter 3, retina illuminating optical system 4', and cornea illuminating optical system 5'.

Except that a variable ND filter 310 for adjusting the amount of light is disposed between the beam splitter 3 and lens 11, the retina illuminating optical system 4' is arranged the same as the retina measuring optical system 4. The diaphragm 13 is disposed conjugately with the retina R and eliminates any other reflected light except light reflected from the retina R as in the first embodiment.

Similarly, except that a variable ND filter 210 for adjusting the amount of light is disposed between the beam splitter 8 and mirror 22, the cornea illuminating optical system 5' is arranged the same as the cornea measuring optical system 5. As in the first embodiment, the optical path length compensating plate 23 serves to compensate each optical path length so as to equalize the total length of the optical path length Lc of the cornea illuminating optical system 5' and the axial eye length [Leye] to the optical path length Lr of the retina illuminating optical system 4', i.e, Lr=Lc+Leye. Lights reflected from the cornea C and retina R each return along its same path and interfere with each other at the beam splitter 3. This interference light is guided to an interference light receiving optical system 400. A reference interference optical system 500 includes a variable ND filter 510 for adjusting the amount of light of the reference laser beam of light, reflecting mirror 520, optical path synthesizing mirror 530 at which the interference light from the beam splitter 3 and the reference laser beam interfere with each other. The interference light receiving optical system 400 includes an image forming lens 410' and light receiver (second light receiving means) 420. The light receiver 420, which outputs signals according to the intensity of an interference fringe, has a light receiving surface 420a. The intensity of the interference light received by the receiver 420 is obtained by adding up the amplitudes of reflected light from the cornea, reflected light from the retina, and reference laser beam and by self-multiplying the sum of the amplitudes. A phase difference between each laser beam depends upon the optical path length between the semiconductor laser 11 and the light receiver 420.

Therefore, the following equations are obtained.

$$Aref = Aref_\phi \cdot exp[i\{\omega t + 2\pi(La + Lref + Ld)/\lambda + \delta\}] \quad (1)'$$

$$Ar = Ar_\phi \cdot exp[i\{\omega t + 2\pi(La + Lt + 2Lr + Li + Ld)/\lambda + \delta\}] \quad (2)'$$

$$Ac = Ac_\phi \cdot exp[i\{\omega t + 2\pi(La + Lt + 2Lc + Li + Ld)/\lambda + \delta\}] \quad (3)'$$

where Aref, At, and Ac are the amplitudes of reference light, reflected light from the retina, and reflected light from the cornea, respectively, $Aref_\phi$, $Ar_\phi$, and $Ac_\phi$ are the maximum amplitudes thereof, respectively, $\delta$ is an initial phase upon emitting a beam from the semiconductor laser 6, La is a distance between the semiconductor laser 6 and beam splitter 150, Lt is a distance between the beam splitter 150 and beam splitter 3, Li is a distance between the beam splitter 3 and beam splitter 530, and Ld is a distance between the beam splitter 530 and light receiver 420.

Comparing Eq. (2)' with Eq. (3)', the difference is Lr and Lc in the term regarding a phase. Since the optical path lengths separated by the optical path length compensating plate 23 are arranged to be equal in the optical paths of the retina and cornea illuminating optical systems 4' and 5', the following equation is obtained:

$$Lr = Lc + Leye$$

A synthetic wave A (A=Aref+Ar+Ac) synthesizing the above three laser beams is now calculated. Suppose that each phase of the lights at the surface 420a of the light receiver 420 is $$\delta r = 2\pi(La + Lt + 2Lr + Li + Ld)/\lambda$$

$$\delta c = 2\pi(La + Lt + 2Lc + Li + Ld)/\lambda$$

$$\delta ref = 2\pi(La + Lref + Ld)/\lambda$$

According to the equations (1)', (2)', and (3)', the synthetic wave A is $$\begin{aligned}A = Ar + Ac + Aref \\ = \sqrt{Ar_0^2 + Ac_0^2 + Aref_0^2 + 2Ar_0Ac_0\cos(\delta r - \delta c) + 2Aref_0 \cdot Ar_0\cos(\delta r - \delta ref) + 2Aref_0 \cdot Ar_0\cos(\delta c - \delta ref)} \\ \cdot exp\{i(\omega t + \delta a)\} \\ = \sqrt{Ar_0^2 + Ac_0^2 + Aref_0^2 + 2Ar_0Ac_0\cos(2\pi \cdot 2Leye/\lambda) + 2Aref_0Ar_0\cos\{2\pi(Lt + 2Lr + Li - Lref)/\lambda\} + 2Aref_0Ac_0\cos\{2\pi(Lt + 2Lc + Li - Lref)/\lambda\}} \cdot exp(i(\omega t + \delta a))\end{aligned} \quad (4)'$$

where Lref is a distance between the beam splitters 150 and 530. The following equation is also obtained.

$$tan\delta = (Ar_\phi sin\delta r + Ac_\phi sin\delta c + Aref_\phi \cdot sin\delta ref)/(Ar_\phi cos\delta r + Ac_\phi cos\delta c + Aref_\phi \cdot cos\delta ref)$$

These two equations explain the amplitude distribution of light wave in space in which the three beams of light are mixed along the optical axis. The term $exp\{i(\omega t + \delta a)\}$ represents a light wave as a progressive wave as a whole. The intensity I of an interference fringe observed at the light receiving surface 420a of the receiver 420 is obtained by self-multiplying the amplitude of the synthetic wave A. The intensity I is $$\begin{aligned}I = Ar_\phi^2 + Ac_\phi^2 + Aref_\phi^2 + 2Ar_\phi Ac_\phi cos(2\pi \cdot 2Leye/\lambda) \\ + 2Aref_\phi Ar_\phi cos\{2\pi(Lt + 2Lr + Li - Lref)/\lambda\} + 2Aref_\phi \cdot Ac_\phi cos\{2\pi(Lt + 2Lc + Li - Lref)/\lambda\}\end{aligned} \quad (5)'$$

In this embodiment, the variation of the intensity in the interference fringe in relation to time is used in the case of a slight variation of the wavelength of the light source.

When the wavelength of the source is successively varied by $\Delta\lambda$, a phase difference of each cos-term, i.e. interference-term of Eq. (5)' is varied. The intensity I' of the interference fringe observed at the surface 420a is $$\begin{aligned}I' = Ar_\phi^2 + Ac_\phi^2 + Aref_\phi^2 + 2Ar_\phi Ac_\phi cos\{2\pi \cdot 2Leye/(\lambda + \Delta\lambda)\} + 2Aref_\phi \cdot Ar_\phi cos\{2\pi(Lt + 2Lr + Li - Lref)/(\lambda + \Delta\lambda)\} + 2Aref_\phi \cdot Ac_\phi cos\{2\pi(Lt + 2Lc + Li - Lref)/(\lambda + \Delta\lambda)\}\end{aligned} \quad (5)''$$

By self-multiplying the sum of the amplitudes after variation, the same intensity as the intensity I' is obtained according to Eq. (4)'. That is, the amount of variation of the intensity I to I' equals the sum of variation of each cos-term of Eq. (5)'' corresponding to each cos-term of Eq. (5)'.

The approximate amount of variation of the phase difference of each cos-term on the condition of the relation $\lambda > \Delta\lambda$ is the fourth term ... $2\pi \cdot 2Leye\Delta\lambda/\lambda^2$ ... (6)' fifth term ... $2\pi(Lt+2Lr+Li-Lref)\Delta\lambda/\lambda^2 \cdots$ (7)' the sixth term ... $2\pi(Lt+2Lc+Li-Lref)\Delta\lambda/\lambda^2 \cdots$ (8)'

The fourth term represents the amount of variation of a phase difference between reflected lights from the retina and cornea; the fifth term the amount of variation of a phase difference between the reflected light from the retina and reference light; and the sixth term the amount of variation of a phase difference between the reflected light from the cornea and reference light.

The amount of variation of the phase difference in (6)' to (8)' is one cycle per $2\pi$. In other words, the intensity of the interference fringe is varied every one period obtained by dividing the amount of variation of each phase difference in (6)' to (8)' by $2\pi$. Therefore, when the wavelength is varied, the variation of the intensity of the interference fringe is observed in the form of the sum of the periodic signals of each interference light varied independently.

To explain briefly, as described in the first embodiment, the wavelength $\lambda$ is linearly varied with respect to time. Supposing that time tm required for the amount of variation $\Delta\lambda$ is 1 second in unit time and $L\Delta\lambda/\lambda^2$ equals 1 in unit optical path difference $L=1$, the following equations are obtained.

$feye = 2Leye$ Hz $fr = Lt+2Lr+Li-Lref$ Hz $fc = Lt+2Lc+Li-Lref$ Hz where feye, fr, and fc are each the frequency of the variation in intensity according to the amount of variation of each phase difference as shown in (6)' to (8)' in correspondence with the variation of the wavelength.

According to Eqs. (5)' and (5)'', the variation in intensity of the interference fringe is obtained in the form of the frequency of a signal formed by mixing signals of the frequencies feye, fr, and fc.

An optical path difference between each beam of light projected onto an eye E to be tested and the reference light is arranged sufficiently longer than the axial eye length Leye here, namely $Lt+2Lr+Li-Lref > 2Leye$ $Lt+2Lc+Li-Lref > 2Leye$ Since $Lr = Lc+Leye$, fr is approximately equal to fc, hence $fr \sim fc$ or $Lt+2Lr+Li-Lref \sim Lt+2Lc+Li-Lref$ where $\sim$ represents an approximation sign.

Therefore, the synthetic signal according to the fifth and sixth terms of (5)' produces a beat the same as in the first embodiment. So, the ratio of the amount of light of the illuminating lights is adjusted by the ND filters 210 and 310. The amount of light of the received light at the receiver 420 is also adjusted by the ND filter 510, whereby the contrast of the beat can be accurately adjusted.

$$fb = fr - fc$$
$$= Lt + 2Lr + Li - Lref - (Lt + 2Lc + Li - Lref)$$
$$= 2Leye$$

and the synthetic frequency $f_0$ thereof is $$f_0 = (fr + fc)/2$$
$$= Lt + 2Lc + Li - Lref + Leye \text{ Hz}$$

This beat signal is observed. The beat frequency fb corresponds to both the amount of variation of the phase difference between the reference light and reflected light from the cornea, and the amount of variation of the phase difference between the reference light and reflected light from the retina.

The signal S observed as a whole is represented as follows.

$$S = Ar_\phi^2 + Ac_\phi^2 + Aref_\phi^2 + 2Ar_\phi Ac_\phi \cos(2\pi \cdot 2Leye \cdot t + \omega 1) + 4Aref_\phi Ar_\phi \cos\{2\pi Leye \cdot t + (\psi 2 - \psi 3)/2\}\cos\{2\pi(Lt+2Lc+Li-Lref+Leye)t + (\psi 2+\psi 3)/2\} \quad (9)'$$

where $\psi 1$, $\psi 2$, and $\psi 3$ are initial phases of output signals corresponding to the fourth, fifth, sixth terms (each regarding interference), respectively, and t is time.

The signal S is produced by mixing the following three signals: a signal of $Ar_\phi^2 + Ac_\phi^2 + Aref_\phi^2$ in bias component; a signal of 2Leye Hz in frequency and $2Ar_\phi Ac_\phi$ in amplitude; and a signal of $Lt+2Lc+Li-Lref+Leye$ in synthetic frequency, $4Aref_\phi Ar_\phi$ in maximum amplitude, and $\cos\{2\pi Leye \cdot t+(\psi 2-\psi 3)/2\}$ in amplitude modulation.

The light receiver 420 outputs a light signal corresponding to the intensity of the interference fringe, i.e., outputs the signal S.

Figure 11:
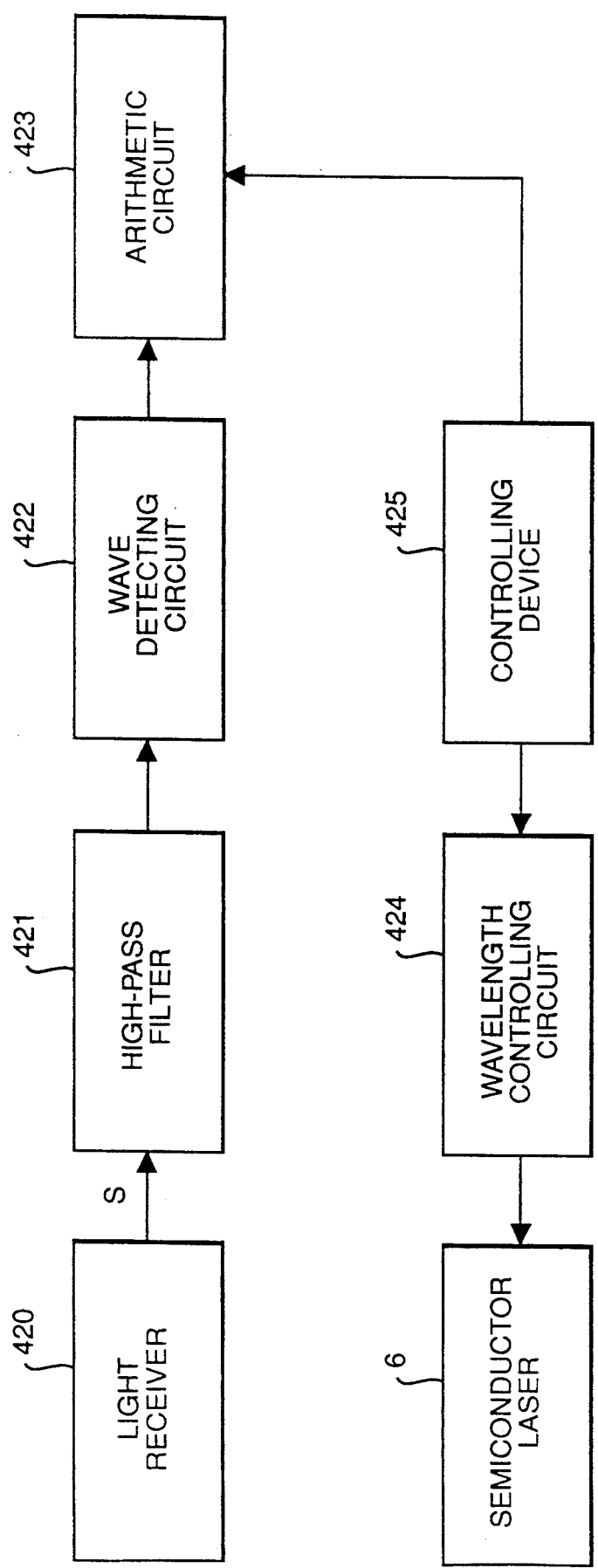
FIG. 11 is a flowchart showing circuits for processing signals to obtain an axial eye length based on a beat signal.

Therefore, the axial eye length $\lceil Leye \rfloor$ is easily obtained with an arithmetic circuit 423 because of the proportion of the beat frequency to only 2Leye such that the signal including bias and low-frequency components as shown in the fourth term of Eq. (9) is eliminated from the signal S outputted from the receiver 420 using a high pass filter 421 as shown in FIG. 11, the signal of the frequency $f_0$ is detected with a detecting circuit 422, and the beat frequency fb is measured. Numeral 424 denotes a wavelength controlling circuit for driving the semiconductor laser 6 and controlling the wavelength of the laser beam. Numeral 425 denotes a controlling device for actuating the wavelength controlling circuit 424 and arithmetic circuit 423. The high-pass filter 421 and detecting circuit 422 each serve as phase difference detecting means for outputting a signal including information about phase differences (hereinafter referred to as a phase difference signal) from the signal S.

Since the frequency of detection signals outputted from the detecting circuit 422, i.e. beat frequency fb corresponding to the amount of variation of a phase difference between the reflected lights from the cornea and retina, a signal processing circuit as shown in FIG. 11 can obtain the axial eye length ⌈Leye⌋ from the amount of variation of the phase difference.

Therefore, the amount of the reference light is arranged larger than that of the reflected light from the cornea (see the fifth term of Eq. (9)′) or reflected light from the retina (see the fourth term of Eq. (9)′) That is, the amplitude $4Aref_\phi Ar_\phi$ of the fifth term is enlarged to increase a difference to the amplitude $2Ar_\phi Ac_\phi$, whereby a light signal sufficient in S/N ratio is outputted from the receiver 420.

For actual measurement, it is necessary to consider that the signal frequency depends upon the wavelength of a laser in actual use, the amount of variation $\alpha\lambda$, and time required for the variation. When a chip temperature of the semiconductor laser 6 is varied as in the first embodiment and thereby the wavelength is varied from $\lambda$ to $\lambda + \Delta\lambda$ during the time period tm linearly with respect to time (see FIG. 13 (a)), frequencies feye, fr, and fc which are each in correspondence with the actual amount of variation of a phase difference are:

$$feye = (2Leye\Delta\lambda/\lambda^2)\cdot 1/tm \qquad (10)'\text{-}1$$

$$fr = (Lt + 2Lr + Li - Lref)\Delta\lambda/\lambda^2 \cdot 1/tm \qquad (10)'\text{-}2$$

$$fc = (Lt + 2Lc + Li - Lref)\Delta\lambda/\lambda^2 \cdot 1/tm \qquad (10)'\text{-}3$$

Since the beat frequency fb = fr − fc, $$fb = 2Leye(\Delta\lambda/\lambda^2)\cdot(1/tm)$$

Therefore, according to the obtained beat frequency fb and the value of $(\Delta\lambda/\lambda^2)\cdot(1/tm)$, 2Leye is found. That is 2Leye is calculated using a reference signal obtained by the reference interference optical system 2 as in the first embodiment.

The amount of variation of a phase difference of the reference interference optical system 2 having a reference length base is measured as follows. The intensity I of the interference fringe observed at the receiver 32 is represented by an equation in which 0 is put in the place of Aref of Eq. (5)′. Namely, $$I = A1^2 + A2^2 + 2A1A2\cos(2\pi \cdot 2Lbase/\lambda)$$

where A1 and A2 are the amplitudes of two lights made incident to the receiver 32 after being reflected from the total reflection mirrors 31 and 32.

When the wavelength of the laser beam is continuously varied by $\Delta\lambda$, the intensity I′ of the interference fringe is $$I' = A1^2 + A2^2 + 2A1A2\cos(2\pi \cdot 2Lbase/(\lambda + \Delta\lambda))$$

Accordingly, the amount of variation $\Delta\delta$ base of a phase difference of the reference interference optical system 2 is $$\Delta\delta base = 2\pi \cdot 2Lbase \cdot \Delta\lambda/\lambda^2 \cdot 1/tm$$

When a signal with the equation $fbase = 2Lbase\cdot\Delta\lambda/\lambda^2\cdot 1/tm$ is outputted from the receiver 32 by unknown values $\lambda$ and $\Delta\lambda$, the frequencies fr and fc, according to Eqs. $fbase = 2Lbase\cdot\Delta\lambda/\lambda^2\cdot 1/tm$, and (10)′-1 to 3, are $$fr = fbase \times (Lt + 2Lr + Li - Lref)/2Lbase$$

$$fc = fbase \times (Lt + 2Lc + Li - Lref)/2Lbase$$

According to the equations fb = fr − fc and Lr = Lc + Le, the frequency fb as a difference between fr and fc is $$fb = fbase \times 2Leye/2Lbase \qquad (11)'$$

Accordingly, since ⌈Lbase⌋ is known, the axial eye length ⌈Leye⌋ can be found the same as in the first embodiment by measuring fb and ⌈fbase⌋. Namely, $$Leye = (Lbase/fbase)\times fb \qquad (12)'$$

The beat frequency fb and the reference frequency ⌈fbase⌋ are measured as follows.

The variation of wavelength is linearly carried out. By synchronous control, signals during the period of the variation tm are inputted in the memory synchronized with the variation of wavelength, as in the first embodiment. The sum of data N during one cycle of the variation is $$N = fad \times tm$$

If one cycle of the signal is composed of the number of data ns, the frequency fs of the signal is $$\begin{aligned} fs &= (N/ns)\cdot 1/tm \\ &= (fad\cdot tm/ns)\cdot 1/tm \\ &= fad/ns \end{aligned}$$

Therefore, by a simultaneous application of this operation to output signals from the reference interference optical system 2 and output signals after detecting the beat signal, fb/fbase is obtained regardless of unknown ⌈fad⌋. Namely, according to the equation fbase = fad/nbs and fb = fad/nb, $$fb/fbase = nbs/nb$$

where nb is the number of data of the reference interference signal during one cycle of the signal and nb is the number of data of the beat signal during one cycle of the signal.

Therefore, between fb/fbase and nbs/nb, the term which is more easily obtained in analysis is calculated.

Figure 12:
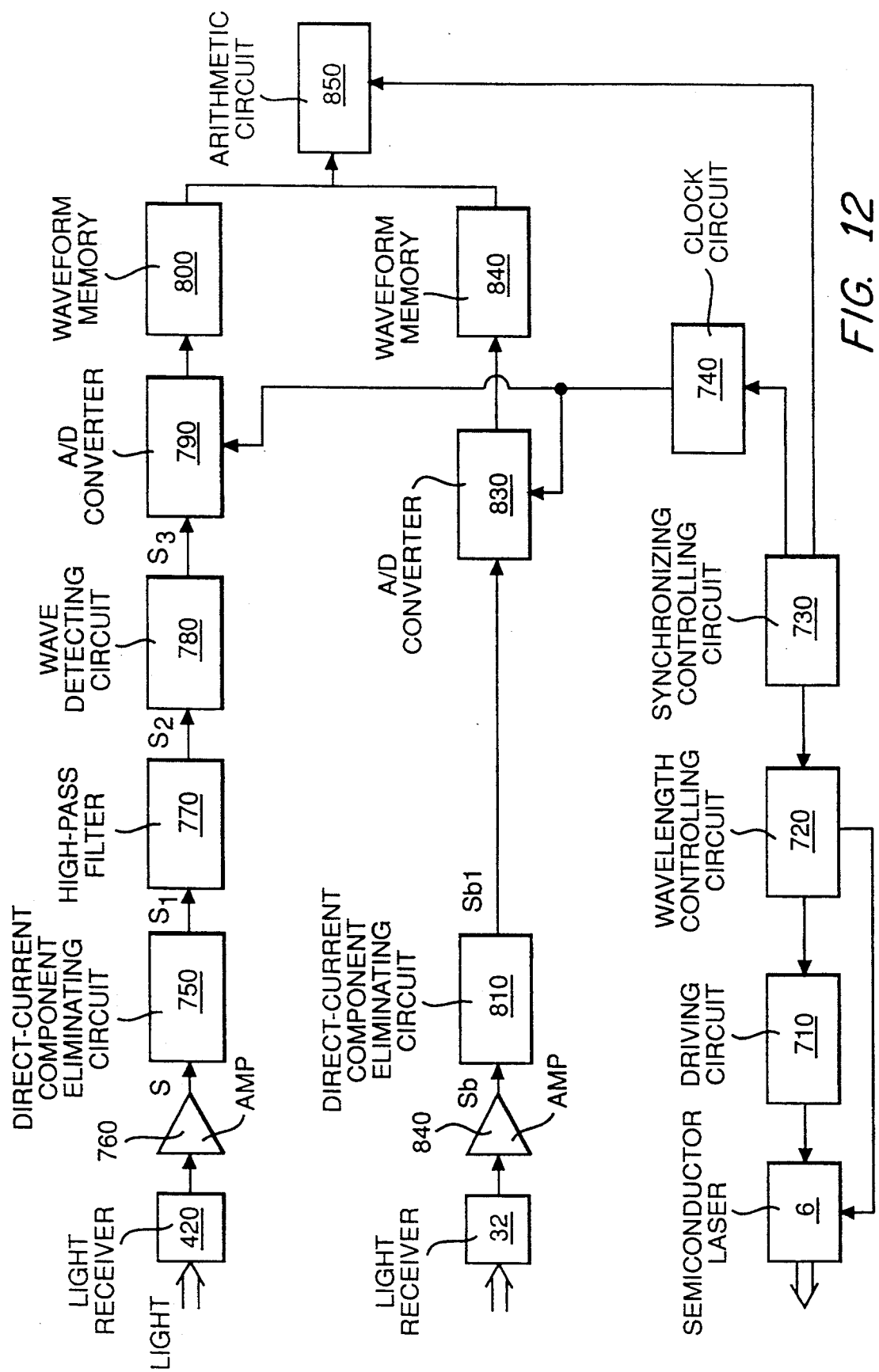
FIG. 12 is a block diagram showing circuits for processing signals to obtain the axial eye length using a reference interference optical system.

FIG. 12 is a block diagram showing a signal processing circuit for measuring the length of an axial eye ⌈Leye⌋.

The arrangement and functions of the circuit will be described hereinafter with reference to the waveforms of FIG. 13.

Figure 13A:
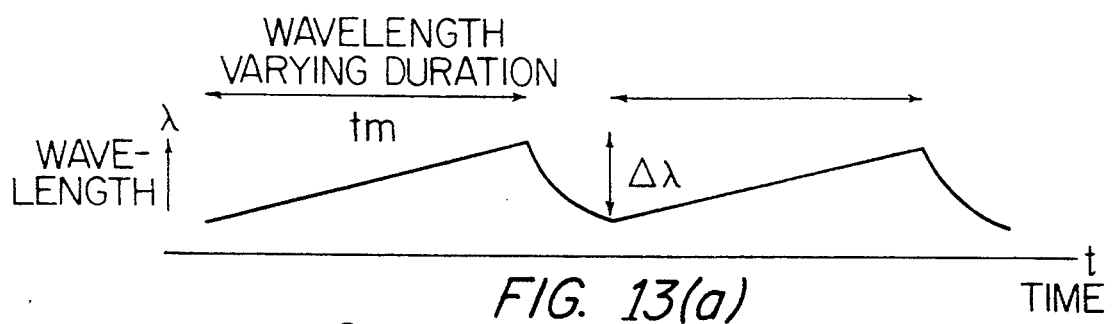
FIGS. 13(a)–13(g) explain waveforms of the signal of the signal processing circuit of FIG. 12.
Figure 13B:
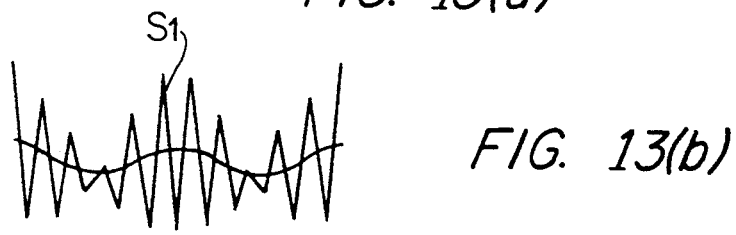
Figure 13C:
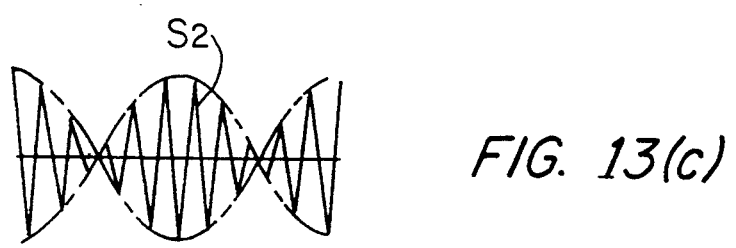

In FIG. 12, the numeral 710 denotes a circuit for driving the semiconductor laser 6. The numeral 720 denotes a wavelength controlling circuit for controlling the chip temperature of the laser 6 in addition to controlling the circuit 710 and for linearly varying the wavelength of a beam of light emitted from the laser 6 during a wavelength varying period tm. The numeral 730 denotes a synchronously controlling circuit for outputting clock signals with a given frequency during a wavelength varying period tm from a clock circuit 740 and for permitting an arithmetic circuit 850 as will be described below to calculate the axial eye length ⌈Leye⌋. The numeral 750 denotes a direct-current component eliminating circuit for eliminating the direct-current components $(Ar_\phi^2 + Ac_\phi^2 + Aref_\phi^2)$ of the light receiving signal S (see Eq. (9)') outputted from the receiver 420 via an amplifier 760 to gain a signal S1 as shown in FIG. 13(B). After eliminating the low-frequency signal ($2Ar_\phi Ac_\phi \cos(2\pi \cdot 2Leye \cdot t + \psi 1)$) as represented in the fourth term of Eq. (9)' by a high-frequency pass filter 770 from the signal S1, a signal S2, as shown in FIG. 13(C), having fr and fc components and corresponding to the phase difference signal is obtained.

Figure 13D:
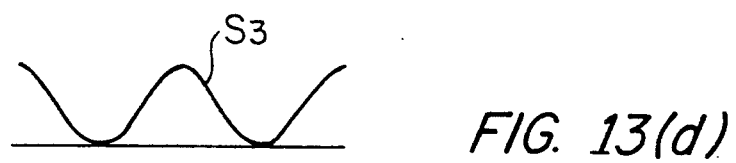
Figure 13E:
Figure 13F:
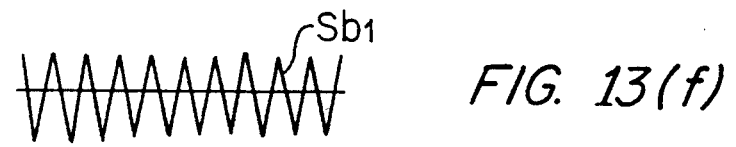

A signal S3 of the beat frequency fb (fb=fr-fc) as shown in FIG. 13(D) is obtained from the signal 52 by the detection of a detecting circuit 780. The direct-current component eliminating circuit 750, the high frequency pass filter 770 and the detecting circuit 780 include phase difference detecting means. An A/D (analogue to digital) converter 790 successively converts the value of the amplitude of the signal S3 into a digital signal synchronizing with the clock signal outputted from the clock circuit 740. A waveform memory 800 stores the A/D converted digital signal as a digital value, as shown in FIG. 13(E), corresponding to the amplitude value. As shown in FIG. 13(F), the light receiving signal Sb outputted from the light receiver 32 via the amplifier 820 ($Sb = A1^2 + A2^2 + 2A1A2 \cdot \cos(2\pi \cdot 2Lbase \cdot t + \psi 1)$) according to Eq. (9)') becomes a signal Sb1 with the frequency ⌈fbase⌋ by eliminating the direct-current component ($A1^2 + A2^2$) by the circuit 810. Synchronizing with the clock signal outputted from the clock circuit 740, the signal Sb1 is converted into a digital signal corresponding to the amplitude value thereof by the A/D converter 830.

Figure 13G:

The A/D converted digital signal is stored in a waveform memory 840 as a digital value which corresponds to the amplitude value as shown in FIG. 13(G). By the command of the controlling device 730, the arithmetic circuit 850 cycle-analizes the digital signals stored in the waveform memories 800 and 840 to obtain periodicities tb and tbase of the signals S3 and Sb1, respectively. The number of data during these periodicities, i.e., the number of data nb of the beat signal A/D converted during the periodicity tb and the number of data nbs of the reference interference signal A/D converted during the periodicity tbase are obtained. The ratio Fb/fbase is calculated from these data and the axial eye length is calculated from the value of fb/fbase according to Eq. (12)'.

In this measuring method, since the beat frequency fb depends upon the axial eye length ⌈Leye⌋, the motion of the eyeball, for example is not necessarily regarded as being very serious in the measurement as in the first embodiment.

In Eqs. (10)'-2 and (10)'-3, when the lengths Lr and Lc are each varied by $\Delta L$ due to misalignment, the frequencies fr and fc are varied as in the following equations:

$$fr = \{Lt + 2(Lr + \Delta L) + Li - Lref\}(\Delta\lambda/\lambda^2)/tm$$

$$fc = \{Lt + 2(Lr + \Delta L) + Li - Lref\}(\Delta\lambda/\lambda^2)/tm$$

The synthetic frequency $f_\phi$ is $$f_\phi = \{Lt + 2Lc + Li - Lref + Leye + \Delta L\}(\Delta\lambda/\lambda^2)/tm$$

However, since fr and fc are each varied simultaneously by the same amount, the beat frequency fb as a difference between fr and fc is stable and is not directly influenced by the misalignment.

Therefore, by sufficiently separating each value of $f_\phi$, feye, and fb from each other and using such a high-pass filter as to be able to operate regardless of the variation of the synthetic frequency $f_\phi$, only the frequency fb is obtained with certainty.

The fourth term of Eq. (9)' also has a signal component of the same frequency as the beat frequency fb. As shown in Eq. (9)', since an interference amplitude is determined by multiplying the amplitudes of the two interference lights by each other, the signal amplitude is enlarged in proportion to the amount of light of the reference laser beam in the fifth term representing the interference between the reflected lights from the eye E, i.e. the reflected lights from the retina and cornea and the reference light.

On the other hand, in the fourth term representing the interference between the reflected lights from the retina and cornea, the signal amplitude is enlarged in proportion to the amount of light of the laser beam for projecting onto the eye E. However, for the safety of the eye, it is impossible to project more than a predetermined amount of light thereonto. Therefore, in this embodiment, the signal represented in the fifth term of Eq. (9)' is used in order to lessen the amount of light projected onto the eye and gain a signal with a large S/N ratio. That is, the signal represented in the fifth term of Eq. (9)', which was enlarged in amplitude by the reference light, is outputted from the light receiver 420.

Now, a signal processing circuit is described for finding the axial eye length without linearly varying the wavelength of the laser beam.

Figure 14:
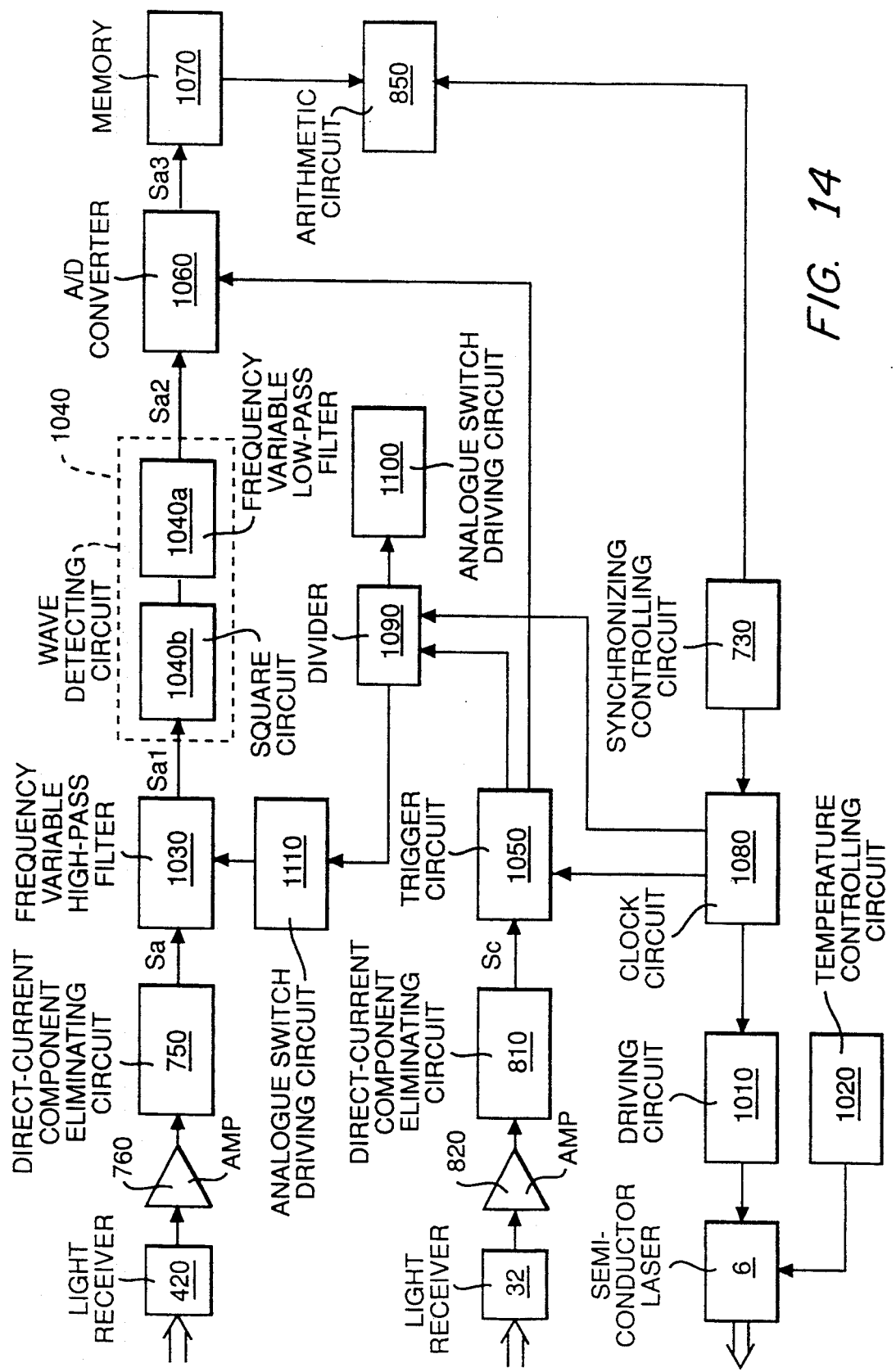
FIG. 14 is a block diagram showing circuits for processing signals of another embodiment of a measuring apparatus in FIG. 12.
Figure 15A:
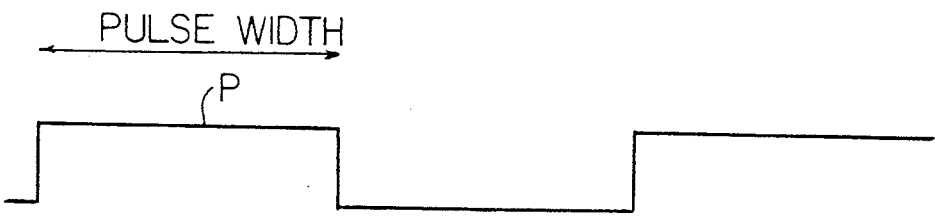
FIGS. 15(a)–15(h) explain waveforms outputted from circuits of a signal processing circuit of FIG. 14.
Figure 15B:
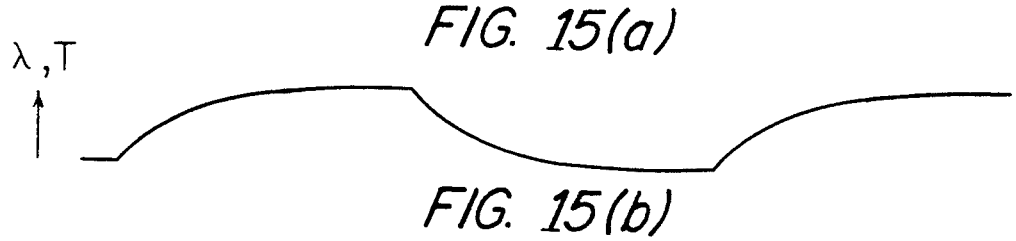

In FIG. 14, the numeral 1010 designates a driving circuit which outputs pulse electric current P (see FIG. 15(A)). By means of the driving circuit 1010, the laser beam emitted from the semiconductor laser 6 is transformed into a rectangular pulse. A chip temperature of the semiconductor laser 6 is varied as in the first embodiment (see FIG. 15(B)). By transferring the semiconductor laser 6 into a pulse form, the average amount of light for projection is lessened and thereby the amount of light for measurement is increased. The pulse width depends upon the width of the variation of wavelength as in the first embodiment.

As in the first embodiment, the reference temperature of the semiconductor laser 6 is controlled by a temperature controlling circuit 1020 as shown in FIG. 14. It may be said that the variation in intensity during a pulse period hardly occurs because the variation in oscillation stabilizes quickly as compared to the variation in temperature. The width of variation of the output as a period from the application of the rectangular input to the stability of the output is not shown in FIG. 15(B). In actual use, it is used after this unstable period. The variation in wavelength in this case is nonlinear so that it is great at the beginning and it gradually calms down.

Figure 15C:
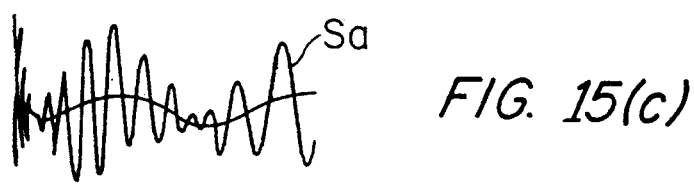

Therefore, the frequency of the obtained signal is very large at the beginning and it gradually decreases. For example, signals Sa and Sc outputted from the direct-current eliminating circuits 750 and 810, respectively, as shown in FIG. 14, are both very high in frequency at the beginning and they gradually becomes low as shown of FIG. 15(C) and FIG. 15(G). After eliminating the low-frequency components by the high-pass filter 1030, the signal Sa is transformed into a signal Sa1 as shown in FIG. 15(D).

Figure 15D:
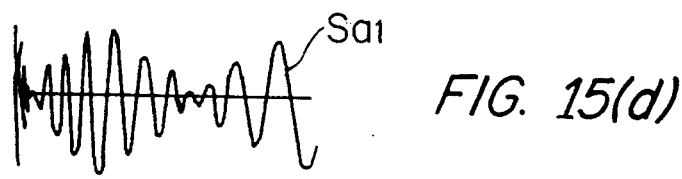
Figure 15E:
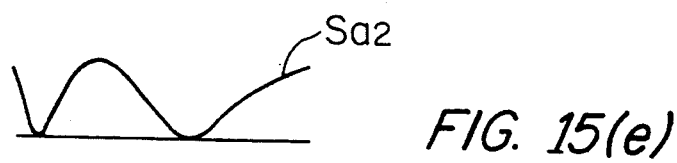
Figure 15F:
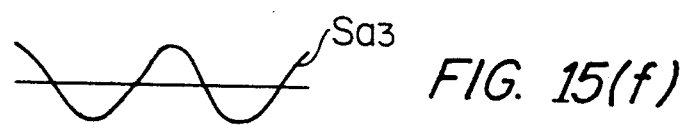
Figure 15G:
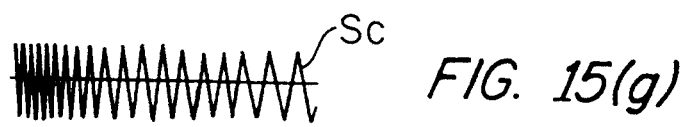

As shown in FIG. 15(D) and FIG. 15(G), the frequencies of these signals Sa1 and Sc also are both large at the beginning and gradually decrease.

Therefore, the frequency fb of the beat signal Sa2 obtained by detecting the signal in FIG. 15(D) with the detecting circuit 1040 is also large at the beginning and it gradually decreases as shown in FIG. 15(E).

Therefore, if the signals Sa2 and Sc in FIG. 15(E) and FIG. 15(G), which are A/D transferred by a trigger with a constant frequency, are regarded as data, the periodicity of each signal is not accurately measured based on the data, as in the first embodiment, because they are each stored as a signal of which the frequency is high at the beginning and becomes lower.

According to Eq. (11)′, the frequency fb of the beat signal and the frequency ⌈fbase⌋ of the signal of the reference interference system 2 have the following relation.

$$fb = fbase \times Leye/Lbase$$

This equation means that fb is constant times as much as fbase on condition that ⌈Leye⌋ and ⌈Lbase⌋ are both stable within the variation period. Therefore, the signal with the frequency ⌈fbase⌋ is used as a trigger for A/D conversion.

Figure 15H:
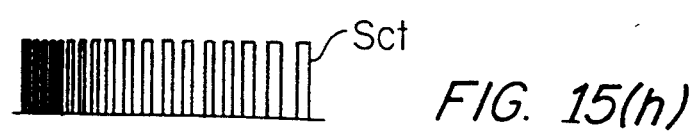

To explain in more detail, the signal Sc with the frequency ⌈fbase⌋ outputted from the direct-current component eliminating circuit 810 as shown in FIG. 14 is outputted in the form of a corresponding trigger signal transformed by the trigger circuit 1050 as shown in FIG. 15(H). A signal Sa2 outputted from the detecting circuit 1040 being synchronized with the output of the trigger signal Sct is transferred by the A/D converter 1060.

Since the ratio of the frequency of the signal Sa2 for A/D conversion to the frequency of the trigger signal is stable, a signal Sa3 obtained thereby is stored as a signal with a constant frequency in the memory 1070 as shown in FIG. 15(F). The value fb/fbase is directly found by measuring the number of triggers, i.e., the number of data (including fractions) composing one cycle of the signal Sa3 because fb/fbase equals the latter, whereby the axial eye length ⌈Leye⌋ is obtained according to Eq. (11)′.

When such frequency variable signal is filtered to eliminate noises thereof or is detected, the high-pass filter 1030 for eliminating noises or the low-pass filter 1040a of the detecting circuit 1040 is required variation of the characteristics together with to vary the signal frequency.

For example, in the case of the initial and final durations of the pulse electric current P (see FIG. 15(A)), the noise frequency for the initial duration is higher than the signal frequency f∅ for the final duration, or the beat frequency fb for the initial duration is higher than the noise frequency for the final duration. If the high-pass filter 108 is arranged to transmit the signal of the signal f∅ for the final duration, the noise for the initial duration is also permitted to pass through the filter 103. Further, if the low-pass filter 104a is arranged to transmit the beat signal for the initial duration, the signal frequency f∅ for the final duration is permitted to pass through the filter 104a. Therefore, as in the first embodiment, a filter is used in which a cutoff frequency fcut is varied in correspondence with the variation of the frequencies (see FIGS. 6 to 8).

Using a signal gained by dividing a clock pulse outputted from the clock circuit 1080 (see FIG. 14) with the divider 1090 or a trigger signal outputted from the trigger circuit 1050, switching on or off of analog switches S1 to S6 is carried out by forming a rectangular signal as shown in FIG. 7 and controlling an analog switch driving circuit 1100.

The cutoff frequency fcut is arranged to be high for the initial duration and becomes lower in accordance with the variation in frequency of the signal (see FIG. 8). The variation of the cutoff frequency is arranged to be in response to the variation of the frequency for process. Since, for the initial duration of the pulse P, the frequency of the signal required to process is also varied quickly, the cutoff frequency is allowed to be varied quickly for the initial duration and be varied slowly for the final duration of the pulse P.

The high-pass filter 1030 is constituted by exchanging the output for the input of the low-pass filter 1040. However, since the capacitance of a capacitor and the value of a combined resistance depends upon the setting of the cutoff frequency fcut thereof, the two filters are not necessarily the same. The beat signal fb obtained by such a filter is converted as mentioned above to measure the value fb/fbase.

In actual measurement in all embodiments, data of a plurality of pulses P, such as 128 pulses, are stored, a judgment on whether a signal of each pulse is present or not is formed, and the pulse including a signal is averaged together with a signal phase in order to obtain a high S/N ratio. The value fbase/fb is found by analyzing the period. The numeral 1110 denotes an analog switch driving circuit similar to that of the numeral 1100, and the numeral 1040b denotes a square-law circuit.

In this embodiment, it has been described that the reflected light from the cornea passes through only the cornea illuminating optical system 5′ and the reflected light from the retina passes through only the retina illuminating optical system 4′. However, as in the first embodiment, such reflected light, as will be described below, may trespass on the optical systems. For example, a part of the light projected onto the retina is reflected from the cornea and it reaches the light receiver 420 via the cornea illuminating optical system 5′ (this part, of the reflected light is hereinafter referred to as R1′). Similarly, a part of the light illuminating the cornea reaches the retina and it is reflected therefrom and it reaches the light receiver 420 via the retina illuminating optical system 4′ (this light is R2′). Further, each part of the reflected lights from the retina and cornea reaches the light receiver 420 via each other's optical path (these lights from the retina and cornea are R3′ and R4′, respectively). These reflected lights may also interfere with each other.

By way of countermeasures against such interference, the optical path lengths between the beam splitters 3 and 16 of the cornea and retina illuminating optical systems are arranged to be equal to each other, so that the laser beam projected onto the eye has no phase difference at the cornea and thereby the phase difference between the reflected lights from the eye becomes zero or results from the axial eye length 2Leye only.

Therefore, since the signal frequency obtained from the interference is limited to fr and fc as each described above and to feye produced by the interference between the reflected lights from the retina and cornea, the axial eye length can be found without changing the signal processing as described above.

The optical system as shown in this embodiment may be changed as follows.

Figure 10:
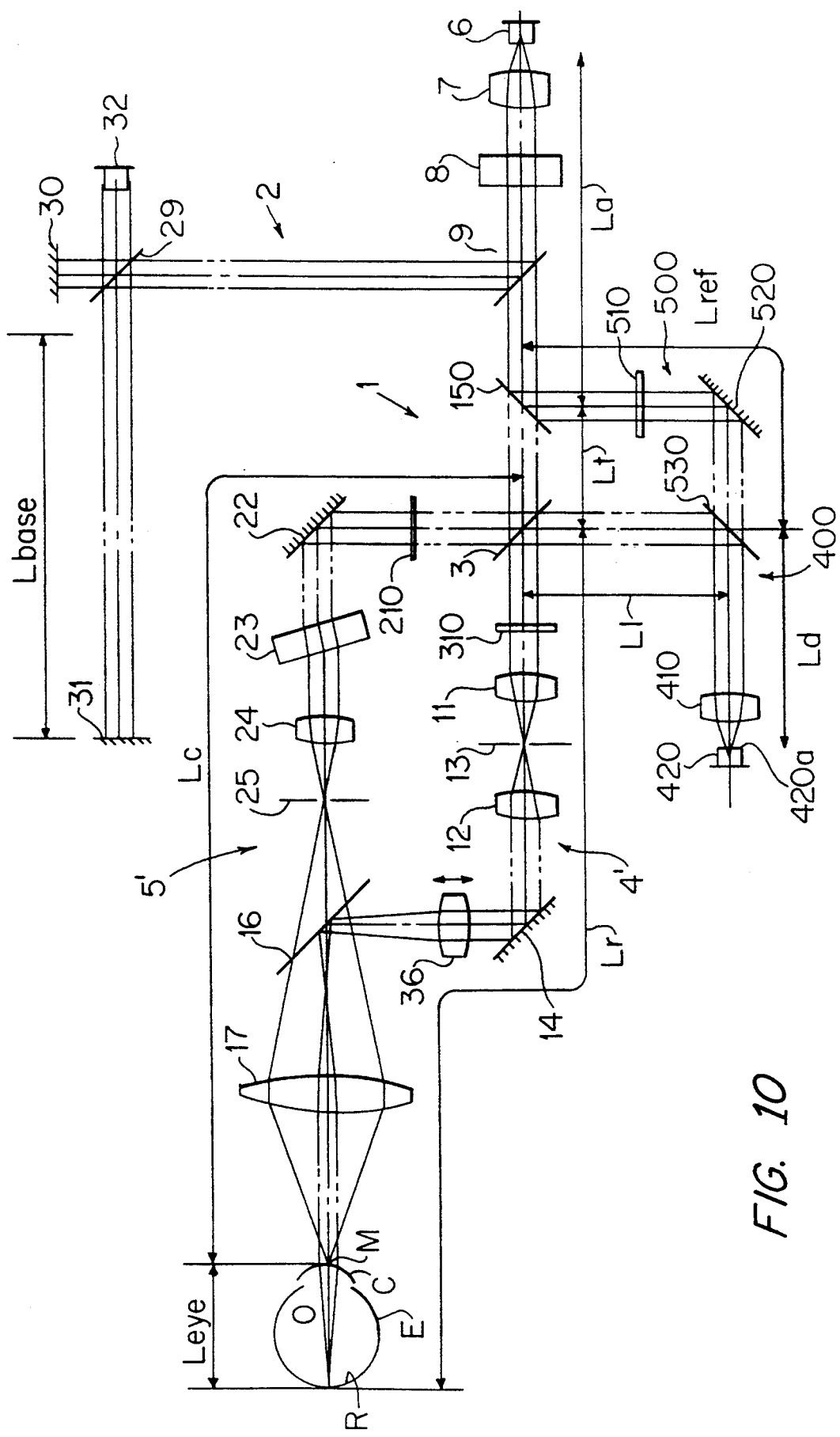
FIG. 10 is a view showing an optical system of a second embodiment of the present invention.

In FIG. 10, the beam splitter 16 is replaced with a polarized beam splitter 16', a λ/2 plate is inserted between the beam splitters 9 and 150, and a beam of light having the plane of polarization inclined at 45 degrees with respect to the drawing sheet is guided to the measuring interference optical system 1. Accordingly, the laser beam emitted from the semiconductor laser 6 with the inclined plane by 45 degrees reaches the polarized beam splitter 16' via the cornea and retina illuminating optical systems 5' and 4'.

Since the polarized beam splitter 16' transmits P-components parallel to the incident surface (the surface of the drawing sheet here) and reflects S-components vertically thereto, only the light with P-components of the illuminating light which passes through the cornea illuminating optical system 5' passes through the polarized beam splitter 16' and illuminates the cornea C.

On the other hand, only the light with S-components of the illuminating light which passes through the retina optical system 4' is reflected from the polarization beam splitter 16' and illuminates the retina R.

The reflected light from the cornea C again reaches the polarization beam splitter 16', a part of the reflected light with polarization passes through the beam splitter and is returned to the cornea illuminating optical system 5', and it becomes incident to the interference optical system 400. On the other hand, the reflected light from the retina R again reaches the polarization beam splitter 16', a part of the reflected light with polarization is returned to the retina illuminating optical system 4', and it becomes incident to the interference optical system 400. The reference light including P and S-components is allowed to interfere with these reflected lights and received by the light receiver 420.

Such arrangement enables a loss of the amount of light at the beam splitter 16 to be lessened because the reflected light from the cornea reserves a large amount of polarized light and the reflected light from the retina tends to do so.

A polarizer may be interposed in the direction of P-polarization for the cornea illuminating optical system and in the direction of S-polarization for the retina illuminating optical system.

Since P and S-polarized lights do not interfere with each other, the reflected lights from the retina and cornea which each have polarized light do not interfere with each other. Therefore, the amount of the interference light represented in the fourth term of Eq.(9)' can be lessened. An exchange of P-polarization with S-polarization is allowed as a matter of course.

In the above arrangement, the reflected light from the cornea is the illuminating light converged upon the apex M in the cornea illuminating optical system 5'. If the surface of the cornea is regarded as spherical, the reflected light converged upon the center of curvature passes through the diaphragm 25 as in the first embodiment.

Figure 16:
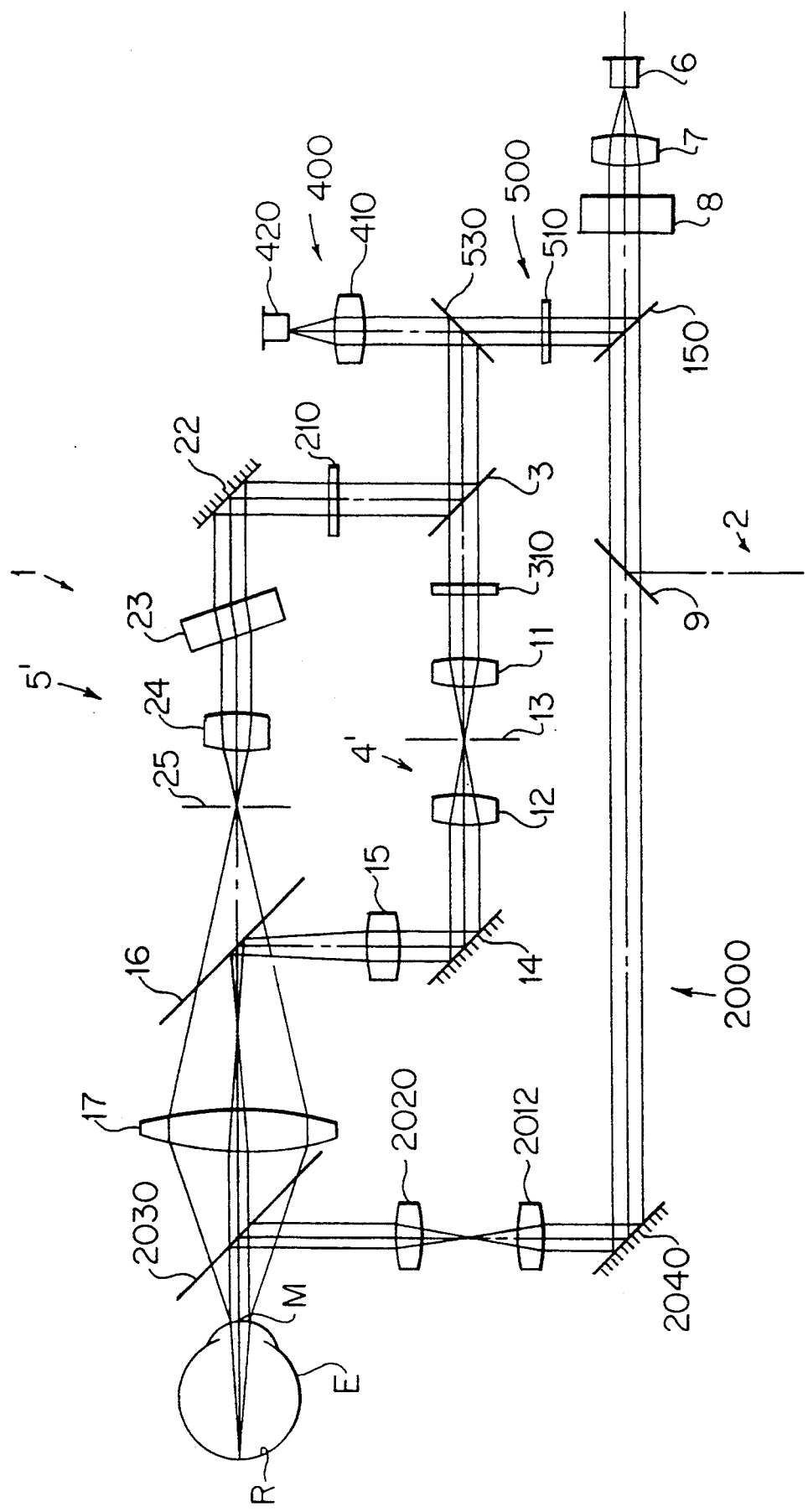
FIG. 16 is a view showing an optical system of a third embodiment of the present invention.

FIG. 16 shows a third embodiment in which a laser beam to be projected onto the eye E is unified.

The numeral 2000 denotes an illuminating optical system to project a laser beam emitted from the semiconductor laser 6 onto the eye E. This optical system 2000 includes refractive power correcting lenses 2010 and 2020 to correct a refractive index of the eye E and converge the light upon the retina. The corrected light is projected onto the eye E via a beam splitter 2030. A part of the projected light is reflected from the surface of the cornea and the other part reaches the retina R and is reflected therefrom.

As in the first embodiment, a measuring interference optical system 1 includes an optical system for the cornea 5' and an optical system for the retina 4'. The measuring interference optical system 1 guides the reflected light from the eye E to an interference light receiving optical system 400.

A different point from the foregoing is that when a virtual image formed by the reflected light from the cornea is in conjugate with the diaphragm 25, the reflected light from the cornea passes through the diaphragm 25 and reaches the interference light receiving optical system 400. When parallel rays of light, for example, are projected onto the eye E, the virtual image is formed at the middle between the surface of the cornea and the center of curvature if the cornea is regarded as spherical. The reflected lights from the cornea and retina and the reference light guided to the interference light receiving system 400 in such a manner interfere with each other. A similar signal processing in the second embodiment is carried out and the axial eye length is calculated. However, since the optical path difference, for example, in the third embodiment is different from that in the second embodiment, some amendments to the formula for calculation are required as follows.

The phase of the reflected light from the cornea at the receiver 420 is $$2\pi(Li+Lc+Lj+Ld)/\lambda;$$

the phase of the reflected light from the retina at the receiver 420 is $$2\pi(Li+Leye+Lr'+Lj+Ld)/\lambda;$$

and the phase of the reference light is $$2\pi(Lref+Ld)/\lambda$$

where Li is an optical path length between the center of the beam splitter 150 and the cornea C, Lr' (Lc) is an optical path length between the cornea and the beam splitter 3, Lj is an optical path length between the beam splitter 3 and the beam splitter 530, Ld is an optical path length between the beam splitter 530 and the light receiver 420, and Lref is an optical path length between the beam splitters 150 and 530. An initial phase is omitted here.

By arranging the optical system to be Lr'=Lc, the axial eye length is obtained in the same manner as in the second embodiment.

While the reflected lights from the cornea and retina are independently guided to the receiver 420 via each proper optical path in the second embodiment, they are unified in the third embodiment so that the reflected lights from the cornea and retina interfere effectively with each other. The amount of the light projected onto the eye E and the amount of reflected light therefrom are adjusted to equalize each amount of light received by the light receiver 420. The equalization allows a clearer contrast in beating.

Figure 17:
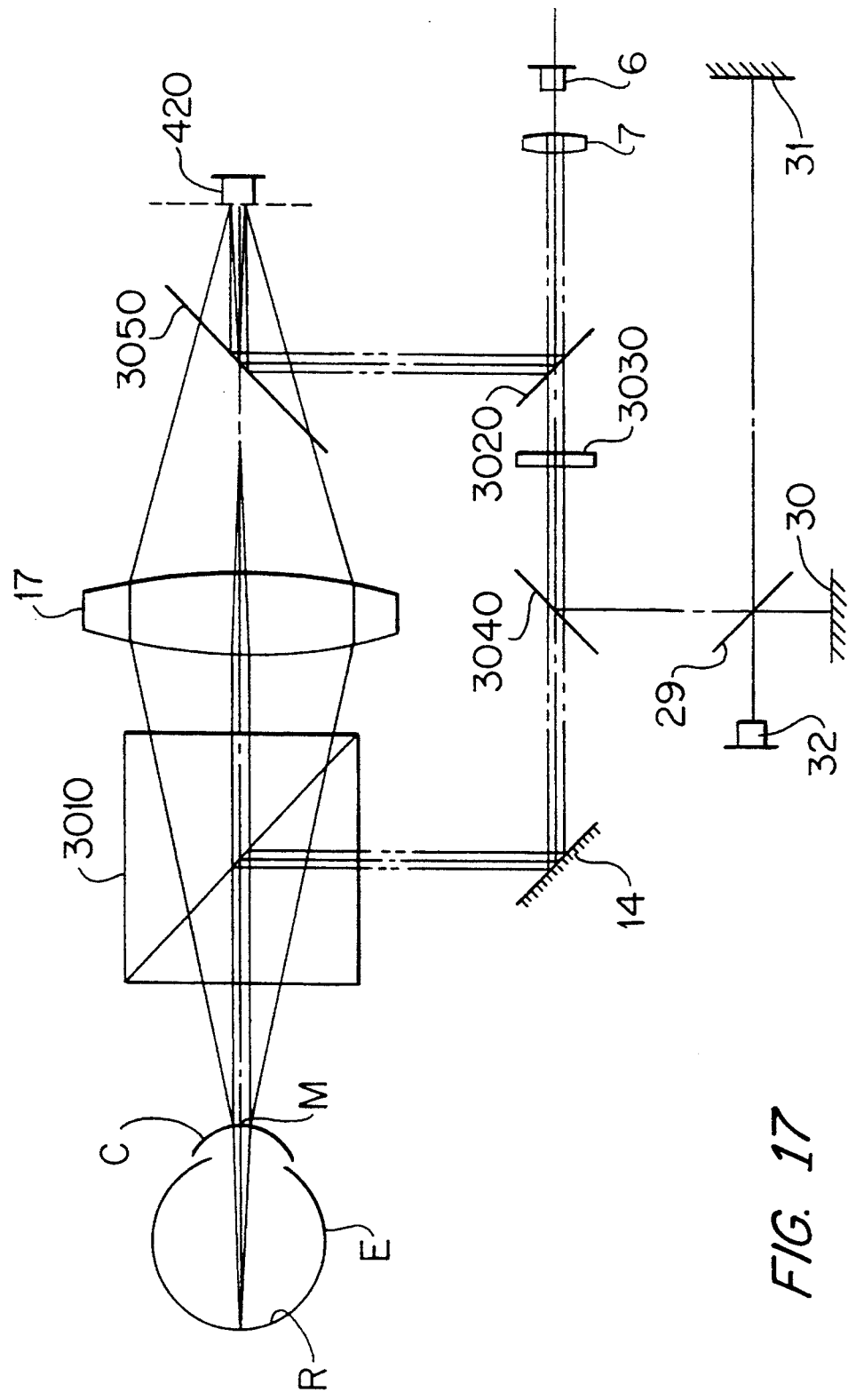
FIG. 17 is a view showing an optical system of a fourth embodiment of the present invention.

FIG. 17 shows a fourth embodiment.

In the fourth embodiment, since an arrangement is made such that only signal components except bias components, are used in the controlling circuits, the contrast is not necessarily enlarged.

Therefore, the optical system may be arranged so that light to project onto the eye E is unified, the reflected lights from the cornea and retina are guided to the light receiving optical system via the objective lens 17, and they are received at such a point as to be each the same light in radius.

In FIG. 17, the numeral 3010 denotes a polarization beam splitter, the numerals 3020, 3040, and 3050 denote beam splitters, and the numeral 3030 denotes a λ/2 plate.

Similar to FIG. 10, the light from the same light source is used and the optical path of the reference light is arranged to be as short as possible in comparison with the optical path passing by the eye E.

In actual use, no difference between the optical path lengths of the illuminating optical systems for the cornea and retina is not required although the optical path difference compensating plate 23 is interposed in order to remove the difference in the second embodiment. The reason is that the axial eye length can be obtained by adding the measured difference between the optical path lengths to the final measured value or subtracting the difference from it. That is, according to the equation $Lr = Lc + Leye + \alpha$ where $\alpha$ is the difference between the optical path lengths of the illuminating optical systems for the cornea and retina, $2(Leye + \alpha)$ is first measured and the difference $\alpha$ is subtracted from the measured value $2(Leye + \alpha)$ to find the axial eye length $\lceil Leye \rfloor$.

What is claimed is:

1. An apparatus for measuring an axial length of an eye having an eyeball, a cornea and a retina comprising:
   a measuring optical system having a coherent light source, said coherent light source projecting monochromatic coherent light having a variable wavelength onto the eyeball, said measuring optical system including a retina optical for projecting said coherent light onto the retina of said eyeball and receiving light reflected from said retina, said retina optical system having a retina reference surface to reflect the coherent light as retina reference light, and a light receiver for receiving interference light between said reflected light from the retina and the retina reference light; and
   a cornea optical system for projecting said coherent light onto the cornea of said eyeball and for receiving light reflected from said cornea, said cornea optical system having a cornea reference surface to reflect the coherent light as cornea reference light, and a light receiver for receiving interference light between said reflected light from the cornea and the cornea reference light;
   means for varying the wavelength of the coherent light and means for mixing interference signals outputted from said corresponding light receivers of the retina optical system and the cornea optical system;
   means for obtaining beat signals according to the varying means and the mixing means; and
   means for calculating an axial eye length according to the beat signals.

2. An apparatus for measuring an axial length of an eye having an eyeball, a cornea and a retina comprising:
   an optical system having a coherent light source, said coherent light source projecting monochromatic coherent light having a variable wavelength;
   a beam splitter for splitting the optical system into a reference interference optical system and a measuring optical system, said reference interference optical system having a longer optical-path difference than the axial eye length;
   said measuring optical system including:
      a retina optical system for projecting coherent light onto the retina and for receiving light reflected from said retina, said retina optical system having a retina reference surface to reflect the coherent light as retina reference light, and a light receiver for receiving interference light between said reflected light from the retina and the retina reference light corresponding to the retina; and
      a cornea optical system for projecting coherent light onto the cornea of said eyeball and for receiving light reflected from said cornea, said cornea optical system having a cornea reference surface to reflect the coherent light as cornea reference light, and a light receiver for receiving interference light between said reflected light from the cornea and the cornea reference light corresponding to the cornea;
   said reference interference optical system including a light receiver for outputting reference interference signals by receiving reference interference light;
   means for varying the wavelength of the coherent light and means for mixing interference signals outputted from said corresponding light receivers of the retina optical system and the cornea optical system;
   means for obtaining beat signals according to the varying means and the mixing means; and
   means for calculating an axial eye length according to said reference interference signals and beat signals.

3. An apparatus for measuring an axial length of an eye having an eyeball, a cornea and retina comprising:
   a measuring optical system having a coherent light source, said coherent light source projecting monochromatic coherent light having a variable wavelength onto the eyeball, said measuring optical system comprising:
   a retina optical system for projecting the coherent light onto the retina of said eyeball and for receiving light reflected from said retina, said retina optical system having a retina reference surface to reflect the coherent light as retina reference light;
   a cornea optical system for projecting the coherent light onto the cornea of said eyeball and for receiving light reflected from said cornea, said cornea optical system having a cornea reference surface to reflect the coherent light as cornea reference light; and
   a light receiver for receiving a first interference light between said light reflected from the retina and said retina reference light, and a second interference light between said light reflected from the cornea and said cornea reference light;
   means for calculating an axial eye length according to beat signal, said beat signals being obtained by varying the wavelength of said coherent light.

4. An apparatus for measuring an axial length of an eye having an eyeball, a cornea and a retina comprising:
   a projecting optical system having a coherent light source, said coherent light source projecting monochromatic coherent light having a variable wavelength onto the eyeball; and
   a measuring optical system for receiving light reflected from said eyeball;
   said measuring optical system comprising:

a retina optical system for receiving light reflected from the retina of said eyeball; and a cornea optical system for receiving light reflected from the cornea of said eyeball;

said projecting optical system comprising:

a retina reference light optical system for guiding retina reference light to said retina optical system; and a cornea reference light optical system for guiding cornea reference light to said cornea optical system;

said retina optical system including a light receiver for receiving interference light between said reflected light from the retina and said retina reference light;

said cornea optical system including a light receiver for receiving interference light between said reflected light from the cornea and said cornea reference light;

means for varying the wavelength of the coherent light and means for mixing interference signals outputted from said corresponding light receivers of the retina optical system and the cornea optical system;

means for obtaining beat signals according to the varying means and the mixing means; and means for calculating an axial eye length according to the beat signals.

5. An apparatus for measuring an axial length of an eye having an eyeball, a cornea and a retina comprising:

means for projecting a laser beam of light having variable oscillation wavelengths;

splitting means for splitting said laser beam of light into measuring light and reference light;

measuring interference means for projecting said measuring light onto the eye and inducing interference between light reflected from the cornea of said eye and light reflected from the retina of said eye;

reference light interference means for inducing interference between light interfered by said measuring interference means and said reference light;

light receiving means for receiving interference light caused by said reference light interference means;

phase difference detecting means for outputting phase difference signals corresponding to a phase difference between said reflected light from the cornea and said reflected light from the retina based on light receiving signals outputted from said light receiving means;

wavelength varying means for varying the wavelength of said laser beam of light within a predetermined range; and arithmetic means for calculating the axial length of the eye based on an amount of variation of the phase difference signals outputted from said phase difference detecting means when the wavelength of said laser beam of light is varied by said wavelength varying means.

6. An apparatus for measuring an axial length of an eye having an eyeball, a cornea and a retina comprising:

means for projecting a laser beam of light having variable oscillation wavelengths;

splitting means for splitting said laser beam of light into measuring light and reference light;

measuring interference means for projecting said measuring light onto the eye and for inducing interference between light reflected from the cornea of said eye and light reflected from the retina of said eye;

base interference means having a base interference optical path to cause interference between light reflected from a base object and light reflected from a reference surface corresponding to said base object, an optical path difference between said base object and said reference surface being longer than a distance between the retina and the cornea, a beam splitter for guiding the laser beam of light emitted from said projecting means to said base interference optical path, and first light receiving means for receiving light interfered by said base interference optical path;

reference light interference means for inducing light interfered by said measuring interference means to interfere with said reference light;

second light receiving means for receiving light interfered by said reference light interference means;

phase difference detecting means for outputting phase difference signals corresponding to a phase difference between said reflected light from the cornea and said reflected light from the retina based on light signals outputted from said second light receiving means;

wavelength varying means for varying the wavelength of said laser beam of light within a predetermined range; and arithmetic means for calculating the axial length of the eye based on both an amount of variation of the phase difference signals outputted from said phase difference detecting means and an amount of variation of signals outputted from said first light receiving means when the wavelength of said laser beam of light is varied by said wavelength varying means.

7. A process for measuring an axial length of an eye having an eyeball, a cornea and a retina, the process comprising the steps of:

projecting a monochromatic coherent light having a variable wavelength onto the eyeball;

reflecting light from the cornea;

inducing interference between the reflected light from the cornea and a first reference light to obtain first photoelectric transfer signals;

reflecting light from the retina;

inducing interference between the reflected light from the retina and a second reference light to obtain second photoelectric transfer signals;

forming beat signals by varying the wavelength of the coherent light and mixing the first and second photoelectric transfer signals; and measuring the axial eye length according to the beat signals.

8. A process for measuring an axial length of an eye having an eyeball, a cornea and a retina, the process comprising the steps of:

emitting a laser beam having a viable oscillation wavelength from a laser source;

splitting the laser beam into a measuring light and a reference light;

projecting the measuring light onto the eye;

reflecting light from the cornea;

reflecting light from the retina;

inducing interference between the light reflected from the cornea and the light reflected from the retina to produce a first interference light;

measuring a first axial eye length according to the interference light;

further including an interference between the interference light and the first reference light to produce a second interference light;

photoelectrically transferring the second interference light to obtain light receiving signals;

determining an amount of variation of a phase difference between the reflected light from the cornea and the reflected light from the retina according to the light receiving signals when the wavelength of the laser beam in varied within a predetermined range; and measuring a second axial eye length from the amount of variation of the phase difference.

* * * * *